(12) United States Patent
McCarthy et al.

(10) Patent No.: US 7,763,663 B2
(45) Date of Patent: Jul. 27, 2010

(54) POLYSACCHARIDE-CONTAINING BLOCK COPOLYMER PARTICLES AND USES THEREOF

(75) Inventors: Stephen P. McCarthy, Tyngsborough, MA (US); Balint Koroskenyi, Lowell, MA (US); Robert J. Nicolosi, Tyngsborough, MA (US)

(73) Assignee: University of Massachusetts, Boston, MA (US)

( * ) Notice: Subject to any disclaimer, the term of this patent is extended or adjusted under 35 U.S.C. 154(b) by 1702 days.

(21) Appl. No.: 10/324,825

(22) Filed: Dec. 19, 2002

(65) Prior Publication Data

US 2010/0040883 A1    Feb. 18, 2010

Related U.S. Application Data

(60) Provisional application No. 60/341,980, filed on Dec. 19, 2001, provisional application No. 60/424,415, filed on Nov. 7, 2002.

(51) Int. Cl.
*A61K 47/00* (2006.01)
(52) U.S. Cl. ............. 514/772.1; 514/772; 514/777
(58) Field of Classification Search ................ None
See application file for complete search history.

(56) References Cited

U.S. PATENT DOCUMENTS

| | | | | |
|---|---|---|---|---|
| 4,152,170 A | * | 5/1979 | Nagase et al. | 106/205.1 |
| 4,526,938 A | * | 7/1985 | Churchill et al. | 525/415 |
| 4,533,254 A | | 8/1985 | Cook et al. | |
| 4,618,664 A | * | 10/1986 | Ohnishi | 527/300 |
| 4,908,154 A | | 3/1990 | Cook et al. | |
| 5,152,923 A | | 10/1992 | Weder et al. | |
| 5,374,614 A | | 12/1994 | Behan et al. | |
| 5,401,243 A | | 3/1995 | Borodic | |
| 5,502,045 A | | 3/1996 | Miettinen et al. | |
| 5,510,118 A | | 4/1996 | Bosch et al. | |
| 5,576,016 A | | 11/1996 | Amselem et al. | |
| 5,629,021 A | | 5/1997 | Wright et al. | |
| 5,651,991 A | | 7/1997 | Sugiyama et al. | |
| 5,670,484 A | | 9/1997 | Binder | |
| 5,672,358 A | | 9/1997 | Tabibi et al. | |
| 5,753,241 A | | 5/1998 | Ribier et al. | |
| 5,766,605 A | | 6/1998 | Sanders et al. | |

(Continued)

FOREIGN PATENT DOCUMENTS

EP        0572080 A1    12/1993

(Continued)

OTHER PUBLICATIONS

Galioglu et al. Block/graft copolymer synthesis via ceric salt, Die Angewandte makromolekulare chemie 1994 pp. 19-28.*

(Continued)

*Primary Examiner*—Eric E. Silverman
(74) *Attorney, Agent, or Firm*—McCarter & English LLP

(57) ABSTRACT

The invention relates to new amphiphilic linear block copolymers of polysaccharides and polymers. The amphiphilic linear block copolymers do not form a true solution in water and are able to form micelles in selective solvents. Also disclosed are particles, each of which has a shell and a core, and a diameter of about 1 to 1,000 nanometers, and methods of delivering agents or removing substances, e.g., undesirable substances, from a subject or environment, by using these particles.

11 Claims, 16 Drawing Sheets

U.S. PATENT DOCUMENTS

| | | | |
|---|---|---|---|
| 5,858,410 | A | 1/1999 | Muller et al. |
| 5,925,341 | A | 7/1999 | Cervantes et al. |
| 5,932,562 | A | 8/1999 | Ostlund, Jr. |
| 5,994,414 | A | 11/1999 | Franco et al. |
| 6,007,803 | A | 12/1999 | Mandeville, III et al. |
| 6,039,936 | A | 3/2000 | Restle et al. |
| 6,117,454 | A | 9/2000 | Kreuter et al. |
| 6,165,500 | A | 12/2000 | Cevc |
| 6,203,802 | B1 | 3/2001 | Handjani et al. |
| 6,224,853 | B1 | 5/2001 | Steel et al. |
| 6,312,708 | B1 | 11/2001 | Donovan |
| 6,358,917 | B1 | 3/2002 | Carruthers et al. |
| 6,387,411 | B2 | 5/2002 | Bruce et al. |
| 6,395,029 | B1 | 5/2002 | Levy |
| 6,429,189 | B1 | 8/2002 | Borodic |
| 6,558,941 | B2 | 5/2003 | Zuelli et al. |
| 6,573,241 | B1 | 6/2003 | Bigalke et al. |
| 6,589,588 | B1 | 7/2003 | Wester et al. |
| 6,623,780 | B1 | 9/2003 | Stevens et al. |
| 6,632,440 | B1 | 10/2003 | Quinn et al. |
| 6,670,322 | B2 | 12/2003 | Goodnough et al. |
| 6,688,311 | B2 | 2/2004 | Hanin |
| 6,720,001 | B2 | 4/2004 | Chen et al. |
| 6,861,066 | B2 | 3/2005 | Van de Casteele |
| 6,869,610 | B2 | 3/2005 | Aoki et al. |
| 6,902,737 | B2 | 6/2005 | Quemin |
| 6,939,852 | B2 | 9/2005 | Graham |
| 6,974,578 | B1 | 12/2005 | Aoki et al. |
| 6,974,579 | B2 | 12/2005 | Brin et al. |
| 7,001,602 | B2 | 2/2006 | Schmidt |
| RE39,086 | E | 5/2006 | Carruthers et al. |
| 7,226,605 | B2 | 6/2007 | Suskind et al. |
| 7,228,259 | B2 | 6/2007 | Freund |
| 7,255,865 | B2 | 8/2007 | Walker |
| 7,384,918 | B2 | 6/2008 | Graham |
| 7,507,419 | B2 | 3/2009 | Coleman, III |
| 2002/0034474 | A1 | 3/2002 | Sabel et al. |
| 2002/0048596 | A1 | 4/2002 | Cevc |
| 2002/0098215 | A1 | 7/2002 | Douin et al. |
| 2002/0107199 | A1 | 8/2002 | Walker |
| 2002/0155084 | A1 | 10/2002 | Roessler et al. |
| 2003/0072801 | A1 | 4/2003 | Curatolo et al. |
| 2003/0138465 | A9 | 7/2003 | Douin et al. |
| 2003/0206955 | A1 | 11/2003 | Sonneville-Aubrun et al. |
| 2004/0003324 | A1 | 1/2004 | Uhlig et al. |
| 2004/0009180 | A1 | 1/2004 | Donovan |
| 2004/0009936 | A1 | 1/2004 | Tang et al. |
| 2004/0028635 | A1* | 2/2004 | Chauvierre et al. ...... 424/70.13 |
| 2004/0033202 | A1 | 2/2004 | Cooper et al. |
| 2004/0037853 | A1 | 2/2004 | Borodic |
| 2004/0126397 | A1 | 7/2004 | Aoki et al. |
| 2004/0151741 | A1 | 8/2004 | Borodic |
| 2004/0229038 | A1 | 11/2004 | Cooper et al. |
| 2004/0258501 | A1 | 12/2004 | Gustow et al. |
| 2005/0074466 | A1 | 4/2005 | Suskind et al. |
| 2005/0079131 | A1 | 4/2005 | Lanza et al. |
| 2005/0123897 | A1 | 6/2005 | Cevc et al. |
| 2005/0142150 | A1 | 6/2005 | Graham |
| 2005/0147688 | A1 | 7/2005 | Russell |
| 2005/0175636 | A1 | 8/2005 | Donovan |
| 2005/0196414 | A1 | 9/2005 | Dake et al. |
| 2005/0208083 | A1 | 9/2005 | Annis |
| 2005/0226842 | A1 | 10/2005 | Douin et al. |
| 2005/0249686 | A1 | 11/2005 | Pataut et al. |
| 2006/0018931 | A1 | 1/2006 | Taylor |
| 2006/0057165 | A1 | 3/2006 | Dimitrakoudis et al. |
| 2006/0073208 | A1 | 4/2006 | First |
| 2006/0093624 | A1 | 5/2006 | Graham |
| 2006/0153876 | A1 | 7/2006 | Sanders |
| 2006/0153877 | A1 | 7/2006 | Kozaki et al. |
| 2006/0165657 | A1 | 7/2006 | Bernasconi et al. |
| 2006/0182767 | A1 | 8/2006 | Borodic |
| 2006/0188525 | A1 | 8/2006 | Donovan |
| 2007/0036831 | A1 | 2/2007 | Baker |
| 2007/0116723 | A1 | 5/2007 | Coleman |
| 2007/0148194 | A1 | 6/2007 | Amiji et al. |
| 2007/0178121 | A1 | 8/2007 | First et al. |

FOREIGN PATENT DOCUMENTS

| | | |
|---|---|---|
| WO | WO 96/23409 | 8/1996 |
| WO | WO 99/27918 | 6/1999 |
| WO | WO 00/38653 A1 | 7/2000 |
| WO | WO 00/74658 A1 | 12/2000 |
| WO | WO 01/10413 A2 | 2/2001 |
| WO | WO 02/064112 A2 | 8/2002 |
| WO | WO 02/076441 A1 | 10/2002 |
| WO | WO 03/101483 A1 | 12/2003 |
| WO | WO 2004/006954 A2 | 1/2004 |
| WO | WO 2004/076634 A2 | 9/2004 |
| WO | WO 2004/084839 A2 | 10/2004 |
| WO | WO 2005/020962 A1 | 3/2005 |
| WO | WO 2005/027872 A2 | 3/2005 |
| WO | WO 2006/005910 A2 | 1/2006 |
| WO | WO 2006/050926 A2 | 5/2006 |
| WO | WO 2006/084353 A1 | 8/2006 |
| WO | WO 2006/094263 A2 | 9/2006 |
| WO | WO 2006/138127 A2 | 12/2006 |
| WO | WO 2007/041664 A1 | 4/2007 |
| WO | WO 2007/089454 A2 | 8/2007 |
| WO | WO 2007/103555 A2 | 9/2007 |

OTHER PUBLICATIONS

JP 04351623 Abstract only Dec. 7, 1992.*
Cappel et al., "Effect of Nanoparticles on Transdermal Drug Delivery", *J. Microencapsulation*, 8 (3):369-374, 1991.
Dittgen et al., "Acrylic Polymers, A Review of Pharmaceutical Applications", *S.T.P. Pharma Sciences*, 7 (6):403-437, 1997.
Forster et al., "Micellization of Strongly Segregated Block Copolymers", *J. Chem. Physics*, 104(24):9956-9970, 1996.
Kwon at al., "Enhanced Tumor Accumulation and Prolonged Circulation Time of Micelle forming poly....", *J. Controlled Release*, 29: 17-23, 1994.
Lee et al., "Biomedical Applications of Collagen", *Int'l J. of Pharmaceuticals*, 221:1-22, 2001.
Ma et al., "Two-Dimensional, Shell-Cross-linked Nanoparticle Arrays", *J. Am. Chem. Soc.*, 123:4627-4628, 2001.
Ruland et al., "Influence of Various Penetration Enhancers on the In Vitro Permeation of Amino Acids Across Hairless Mouse Skin", *Int'l. J. of Pharmaceutics*, 85:7-17, 1992.
Stolnik et al., "Long circulating microparticulate drug carriers", *Advanced Drug Delivery Reviews*, 16: 195-214, 1995.
Talingting et al., "Onion-Type Micelles from polystyrene-*block*-poly (2-vinylpyridine) and Poly (2-vinylpyridine)-*block*-poly(ethylene oxide)", *Macromolecules*, 32: 1593-1601, 1999.
International Search Report for Application No. PCT/US06/46236, dated Jun. 17, 2008.
International Search Report for Application No. PCT/US06/26918, dated Jun. 19, 2008.

* cited by examiner

FIGURES

Atomic Force Microscopy Image of cationic hollow nanoparticles.

Poly Caprolactone $M_n$ =9,300

Average Height: 11.3 nm

Average Diameter: 126 nm

POLYSACCHARIDE-CONTAINING BLOCK COPOLYMER PARTICLES AND USES THEREOF

CROSS-REFERENCE TO RELATED APPLICATIONS

This application claims priority from U.S. provisional applications Ser. No. 60/341,980 filed on Dec. 19, 2001 and Ser. No. 60/424,415 filed on Nov. 7, 2002, the contents of which are incorporated herein by reference in their entireties.

TECHNICAL FIELD

This invention relates to novel block copolymers, and particles and uses thereof.

BACKGROUND

Over the past decade, there has been a surge of interest in block copolymers, as well as microparticles and nanoparticles of these block copolymers. These block copolymers are made of synthetic polymer blocks such as polystyrene, poly(ethylene oxide), polyglycolide, polylactide, and polycaprolactone. Examples of the copolymers include polystyrene-co-vinylpyridine, polystyrene-co-polyethylene, polystyrene-co-polylactide, polystyrene-co-polyisoprene, polystyrene-co-polyacrylic acid, poly(ethylene oxide-aspartate), and polycaprolactone-co-polyamide. See, e.g., Forster et al., J. Chem. Phys., 1996, 104, 9956-9970; Ma et al., J. Am. Chem. Soc., 2001, 123, 4627-4628; Talingting et al., Macromolecules, 1999, 32, 1593-1601; Kwon et al., J. Control. Rel., 1994, 29, 17-23; and Stolnik et al., Adv. Drug Deliv. Rev., 1995, 16, 195-214.

SUMMARY

The present invention is based on the discovery that an amphiphilic linear block copolymer can be synthesized from a polysaccharide by reacting it with a polymer such as a polyester, polycarbonate, polyanhydride, polyamide, polysaccharide, poly(β-hydroxy acid), poly(vinyl alcohol), protein, or copolymers of any of these materials.

In general, the invention features an amphiphilic linear block copolymer including a first polymer block and a second polymer block, wherein the first polymer block includes a polysaccharide or derivative thereof. The amphiphilic linear copolymer can form micelles in a selective solvent. The solvent can be or include water, dimethyl sulfoxide, dimethyl acetamide, dimethyl formamide, chloroform, tetramethyl formamide, carbon tetrachloride, N-methylpyrolidone, or dichloroethane.

Another aspect of this invention relates to novel amphiphilic linear block copolymers each having a first polymer block and a second polymer block connected covalently at the chain ends. The first polymer block is hydrophilic (or hydrophobic) and contains a polysaccharide, while the second polymer block is hydrophobic (or hydrophilic). The amphiphilic block copolymers do not form a true solution in water and are able to form micelles in a selective solvent such as water. Embodiments of these amphiphilic linear block copolymers include amphiphilic linear diblock or multiblock copolymers.

"A selective solvent" refers to a solvent in which an amphiphilic diblock copolymer forms micelles, each of which has an interior or core composed of either the hydrophobic or the hydrophilic block of the copolymer (depending on the nature of the solvent), and an exterior or shell composed of the other block of the copolymer. A selective solvent can comprise a single solvent or a combination of two or more different solvents.

Suitable hydrophilic polysaccharides can be composed of simple sugars (or their derivatives) connected by glycosidic bonds, as known in the art. Such sugars include D-glucose, D-mannose, D- and L-galactose, D-xylose, L-arabinose, D-glucoronic acid, D-galactoronic acid, D-mannuronic acid, D-glucosamine, D-galactosamine, neuraminic acid, and their derivatives such as aminated, sulfonated, or carboxymethylated sugars. Other examples of hydrophilic polysaccharides include pullulan, carrageenan (a naturally occurring sulfated polysaccharide), glycon, hydroxycellulose, amylose, chitosan, N,O-carboxymethylchitosan, algin, and alginic acid, starch, dextran, cyclodextrin, konjac glucomannan, chitin, pustulan, heparin, curdlan, hyaluronic acid, and xanthan. These hydrophilic polysaccharides can be modified to become hydrophobic by introducing a large number of side-chain hydrophobic groups. Suitable hydrophobic polysaccharides include chitin, cellulose acetate, pullulan acetate, konjac acetate, amylose acetate, and dextran acetate.

The polymer contained in the hydrophobic polymer block can be a degradable polymer. Suitable degradable polymers include polyesters (e.g., polylactide and polyglycolide), polycarbonates (e.g., poly(1,3-dioxan-2one)), polyanhydrides (e.g., poly(sebacic anhydride)), polyamides (e.g., polycaprolactam), polysaccharides (e.g., hydroxyethylstarch), poly(β-hydroxy acid)s (e.g., poly(β-hydroxyalkanoate)), poly(vinyl alcohol)s, proteins (e.g., collagen), or their copolymers (e.g., polydepsipeptide, a poly(amide-co-ester)). Suitable hydrophobic polyesters include those well known in the art, such as polycaprolactone and their copolymers, e.g., poly(DL-lactide-co-glycolide).

In another aspect, the invention features a method of making an amphiphilic linear block copolymer by obtaining a first molecule including a polysaccharide with ring hydroxyl groups; protecting the ring hydroxyl groups of the polysaccharide; coupling the protected polysaccharide with a second molecule; and removing the protecting groups on the ring-hydroxyl groups. The second molecule can be a degradable polymer including a polyester, polycarbonate, polyanhydride, polyamide, polysaccharide, poly(β-hydroxy acid), poly(vinyl alcohol), or a protein, or copolymers thereof. The second molecule can be a monomer, and the monomer polymerizes into a polymer.

Examples of protecting groups for ring hydroxyls include chloroacetyl chloride, chloroacetyl bromide, chloroacetic anhydride, dichloroacetyl chloride, dichloroacetyl bromide, dichloroacetic anhydride, trichloacetyl chloride, trichloacetyl bromide, or trichloroacetic anhydride. The protecting groups on the ring hydroxyl groups can be removed by hydrolysis.

Another method of making an amphiphilic linear block copolymer includes obtaining a nitrophenyl carbonate derivative of the second polymer block; and reacting the glycosidic hydroxyl of a polysaccharide of the first polymer block with the nitrophenyl carbonate derivative of the second polymer block to form the block copolymer.

Another method of making an amphiphilic linear block copolymer includes converting the reducing end of the polysaccharide chain of the first polymer block into a glycosyl amine obtaining a nitrophenyl carbonate derivative of the second polymer block, and reacting the glycosyl amine with the nitrophenyl carbonate derivative of the second polymer block to from the amphiphilic block copolymer.

"A protecting group" refers to a compound that is used to protect a functional group, e.g., hydroxy, from unwanted reactions, and can be easily removed when it is no longer needed. See, e.g., Greene et al., Protective Groups in Organic Synthesis, 3rd Edition, New York, 1999, for a list of suitable protecting groups.

A further aspect of the invention features a particle including the linear amphiphilic copolymer wherein the particle has a diameter of 1-1000 nanometers, a core made of one block of the copolymer, and a shell made of another block of the copolymer. In some embodiments, the particle may include one or more of the following features. The particle includes a copolymer of a polysaccharide and polycaprolactone. In various embodiments, the particle can have a diameter of 15-100 nm. The shell of the particle can include the first polymer block, and the first polymer block can be crosslinked. In some embodiments, the core of the particle can be removed.

The new particles can be either microparticles or nanoparticles. The terms "microparticles" and "nanoparticles" refer to particles having a diameter of about 200-1,000 nanometers and about 1-200 nanometers, respectively. The size to volume ratio for a particle of size 1 nm is about 1000 times greater than that for a particle of size 1 μm. This large increase in surface area facilitates a much higher absorption of drugs that are loaded into nanoparticles relative to those loaded into microparticles.

In another aspect, the invention features a copolymer wherein the first polymer block can be biologically active, e.g., having antibacterial, antiviral, anticoagulative, anti-cancer, anti-proliferative, anti-atherosclerotic, anti-angiogenic, anti-metastatic, or cholesterol-lowering activity. The copolymer having biological activity can include the first polymer block.

Still another aspect of this invention relates to a method of delivering an agent to a subject such as a mammal (e.g., a human or an animal such as a dog, cat, horse, cow, or pig) or other animals such as fish or birds, by using the above-described particles of amphiphilic diblock copolymers. The agent can be contained within or bound to the surface of the particles. The agent can be a radiodiagnostic substance (e.g., a marker that can be observed by magnetic resonance imaging), a drug, a prodrug, a biologically active substance (e.g., DNA, RNA, a gene sequence, or a protein such as insulin), a material that contains ionizable groups, or a cell, and is encapsulated within or infused into the particles. The core may also contain nutraceuticals such as vitamins (e.g., vitamins E, C, or D) and sterols. Further, the core can contain, in addition to the pharmaceutical and/or nutraceutical to be delivered, a sustained release agent, e.g., phosphatidyl choline or lysophasphatidyl choline, for the controlled release of the pharmaceutical or nutraceutical.

In certain embodiments, the agent can be delivered by systemic administration for delivery to the brain across the blood-brain-barrier. Particles of sufficiently small size and adequate hydrophilicity/hydrophobicity can travel through the blood-brain barrier (BBB). The solubility of particles increases directly as their hydrophilicity and transport across membranes, particularly across the BBB, increases directly as their hydrophobicity increase. Thus, pharmaceutical and nutraceutical agents can be loaded into nanoparticles particles and can be delivered to the brain.

In another aspect, the invention features a method of transdermally delivering an agent to a subject, by administering to the subject one or more particles of amphiphilic block copolymer by contacting the particles to the surface of the subject's skin, wherein the agent is contained within or bound to the surface of the particles. The subject can be a mammal, for e.g., human. The agent can include a biologically active substance, e.g., an antibacterial agent, an antiviral agent, an anticoagulant, an anticancer agent, an anti-inflammatory agent, a contraceptive, a neutraceutical, an inhibitor of an enzyme, an anti-depressive agent, a nucleic acid, vaccine, insulin, or a DNA vaccine.

Also within the scope of the invention is a method of removing a substance, e.g., an undesirable substance, from a fluid by using the particles described herein. The fluid can be within a subject, e.g., a human, or in an environment (e.g., in a pond, lake, stream, or the air). The fluid can be a liquid, such a water, blood, lymph, or cerebrospinal fluid. The fluid can also be air. The method includes administering to the subject, or introducing into the environment, a sufficient amount or number of the particles to sequester the substance, and then removing the particles, thereby removing the substance, which is sequestered within the particles. The substances sequestered can be cholesterol, a bile acid, fat, a metal ion (e.g., $Cu^{2+}$), metals, such as mercury or lead, a toxin (e.g., pesticide, hydrocarbon, or other poison), a complex ion (e.g., phosphate), a bacteria, a virus, a nucleic acid or a pollutant in water or soil. Preferably, the shells of these particles carry charges that would strengthen the binding of the substance to be removed by the particles.

In another aspect, the invention features a method of imaging a disorder in a subject by labeling one or more particles of amphiphilic block copolymer with a reporter group and with a targeting agent that binds to a target associated with the disorder; administering the labeled particles to the subject under conditions and in an amount sufficient to bind to the target; and imaging the reporter group, thereby imaging the disorder, e.g., cancer.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

One advantage of the new copolymers and particles is that, by using a polysaccharide as one block of the copolymers, the particles are not toxic to a subject. In addition, the new copolymers can be readily prepared from renewable resources. Other advantages include ease of cross-linking of the hydrophilic polysaccharide, ease of derivatization (e.g., introducing functional groups such as carboxyl and amine groups), and the possibility for fine-tuning of the hydrophilicity of the new linear block copolymers.

Another advantage is that nanoparticles provide new methods for noninvasive and localized administration of pharmaceutically or biologically desirable substances. It also enables delivery of substances to the brain, since the particles are sufficiently small in size, and have other characteristics, such as a hydrophobic nature, which can be accomplished by functionalizing the particles with fatty acids that enable them to pass through the blood-brain barrier (BBB). The hydrophobicity of the nanoparticles can be increased by attachment of fatty acids to the surface, which increases the ability of the particles to cross the BBB.

The details of several embodiments of the invention are set forth in the description below. Other features, aspects, and advantages of the invention will be apparent from the description, and from the accompanying claims.

DETAILED DESCRIPTION OF THE DRAWINGS

DETAILED DESCRIPTION OF THE INVENTION

Figure 1:
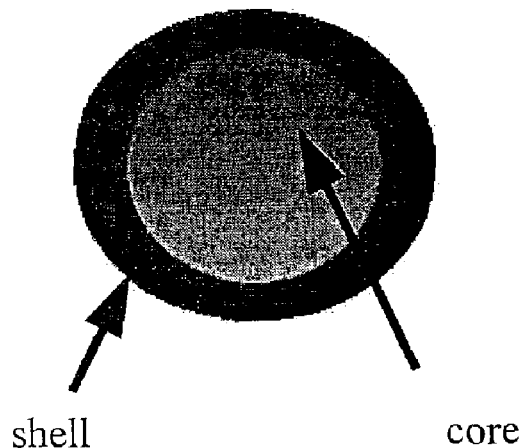
FIG. 1 is a diagram of a particle as described herein. This particle has a core composed of a polymer block and a shell composed of another polymer block.
Figure 2:
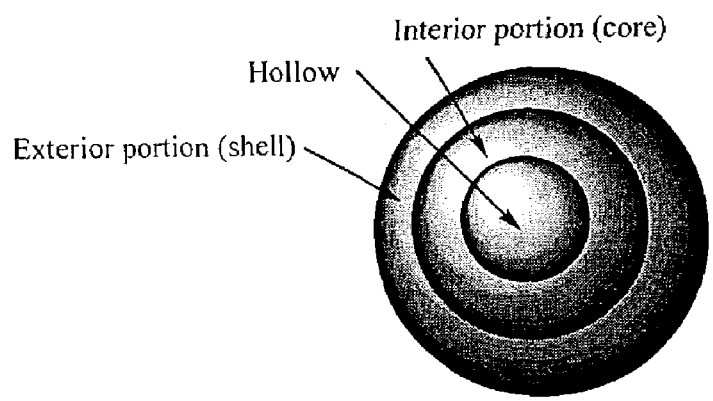
FIG. 2 is a diagram of a particle as described herein. This particle has an exterior portion (e.g., a shell), and an interior portion (e.g., a core), which encompasses a hollow center.
Figure 3:
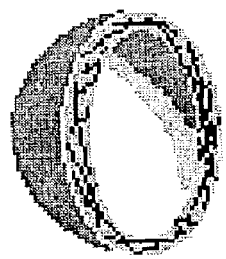
FIG. 3 is a diagram of a particle having a hollow core and a crosslinked shell. The particle is able to swell in a selective solvent.
Figure 4:
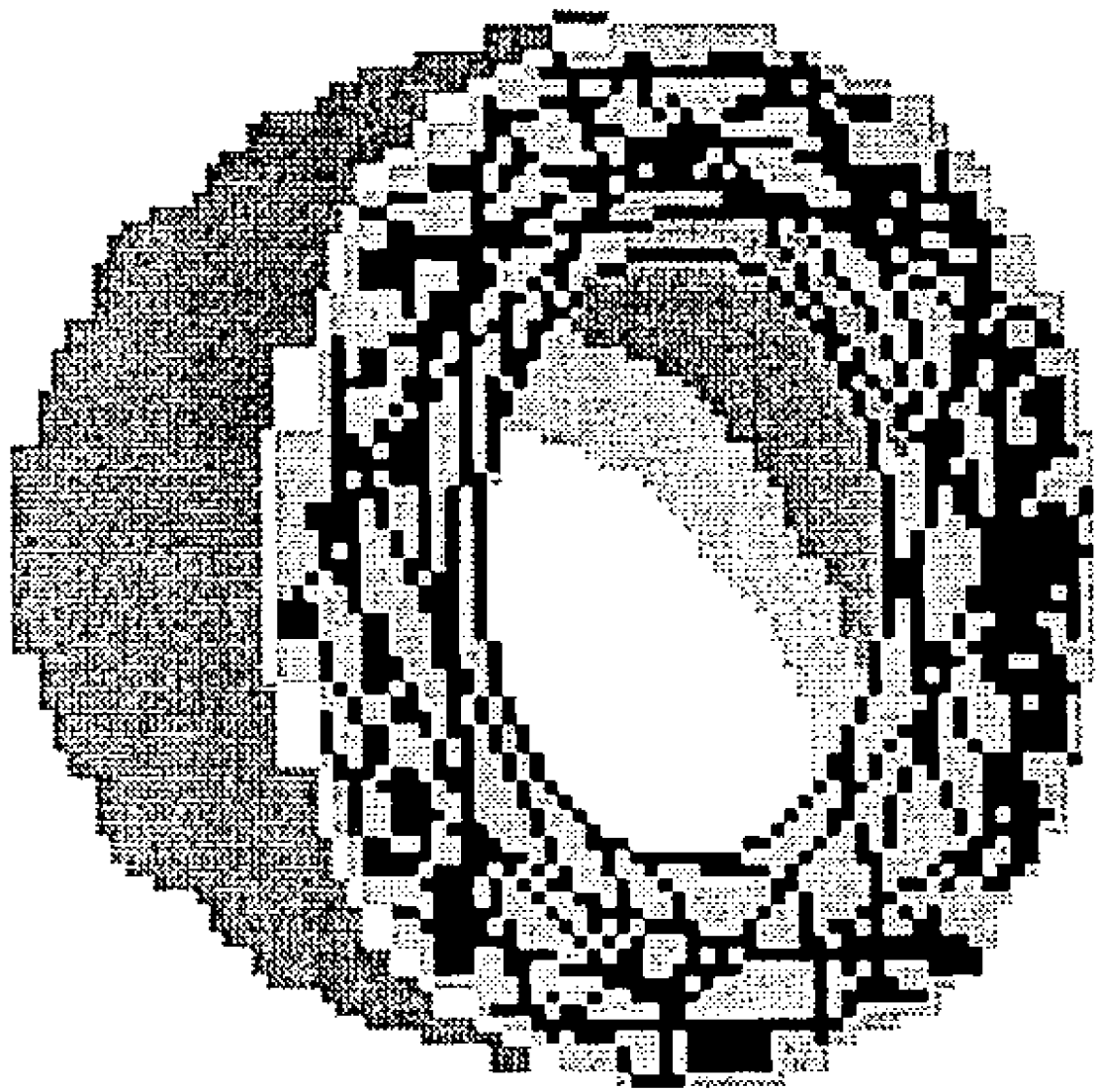
FIG. 4 is a diagram of a particle swollen in a selective solvent. The particle has a hollow core and a crosslinked shell.

The present invention includes novel linear amphiphilic block copolymers, particularly, amphiphilic diblock copolymers. Each of the copolymers contains a polysaccharide. The invention also includes microparticles and nanoparticles made from the amphiphilic copolymers.

Polysaccharides having ring hydroxyl groups are generally hydrophilic. Extensive modifications of these polysaccharides have been carried out, most predominantly by substitution of the hydroxyl groups. Various substituted derivatives of these polysaccharides are also found in naturally occurring polysaccharides, e.g., chitosan (an aminated polysaccharide), alginic acid (a carboxylated polysaccharide), and carrageenan (a sulfated polysaccharide). All of these polysaccharides can be used in the new copolymers.

The microparticles and nanoparticles are fabricated from a polymer, which can be a homopolymer or copolymer, including block and graft copolymers. The method of fabrication can be emulsion polymerization, self-assembly, or any other method that produces nanoparticles. In one embodiment, the shape of the microparticle and nanoparticle can be spherical. Each of the particles has an outer portion or shell made from the hydrophilic (or hydrophobic, depending on the surrounding liquid) block of the copolymer and an interior portion or core made of the hydrophobic (or hydrophilic) block of the copolymer. When a polysaccharide forms the shell, it is optionally crosslinked, chemically (e.g., by using a multifunctional molecule to react with hydroxy groups on the hydrophilic polysaccharide) or physically (e.g., by using a charged ion, such as $Ca^{2+}$, to interact with ionic groups, such as carboxylic groups, on the hydrophilic polysaccharide). The cross-linking reaction can be accomplished using thermal energy or UV radiation. The interior portion (i.e., the core) of each particle can further contain a hollow space within, resulting in either a particle having two levels, i.e., a crosslinked shell and a hollow core within, or a particle having three levels, i.e., the exterior portion or shell, the interior portion or core, and a hollow portion within the core. Further, the core can be physically or chemically crosslinked.

Synthesis of Amphiphilic Linear Block Copolymers

Each of the novel amphiphilic linear block copolymers, e.g., diblock copolymers, includes a hydrophilic polymer block containing a polysaccharide and a hydrophobic polymer block containing a polyester or polysaccharide. Alternatively, each of the novel copolymers includes a hydrophobic polymer block containing a polysaccharide and a hydrophilic polymer block containing a polyester or polysaccharide. The hydrophilic polymer block can further contain other types of hydrophilic polymers such as a polyalkylene oxide (e.g., polyethylene oxide). Likewise, the hydrophobic polymer block can also contain other types of hydrophobic polymers such as polyamides (e.g., polycaprolactam). Different synthetic schemes might be required for polysaccharides that do not contain ionic groups in the sugar rings (i.e., a charge-free polysaccharide) and for polysaccharides that contain ionic groups on the sugar rings (i.e., a charged polysaccharide).

To synthesize an amphiphilic diblock copolymer, a suitable hydrophilic polysaccharide (e.g., amylose or pullulan) can be first treated with a protecting group (e.g., chloroacetyl chloride) to protect ring hydroxyl groups on the polysaccharide. The protected polysaccharide can then be coupled at one end with a suitable hydrophobic polymer (e.g., a polyester or a polyamide) or polysaccharide bearing a hydroxyl group on the chain end. Alternatively, the protected polysaccharide can be subjected to copolymerization also at only one end with a monomer, which polymerizes into a hydrophobic polymer (e.g., a polyester or a polysaccharide), to obtain a new amphiphilic diblock copolymer. After the coupling reaction or the copolymerization, the protecting groups on the hydrophilic polysaccharide are removed, e.g., by hydrolysis under mild conditions.

Alternatively, the polysaccharides can be used for the coupling reaction without protecting the hydroxyl groups. In this case, the glycosidic hydroxyl of the polysaccharide is either used directly or converted into a glycosyl amine, which is then reacted with the nitrophenyl carbonate derivative of the hydrophobic polymer.

For a charged hydrophilic polysaccharide, an esterification step can precede the protecting step before the polysaccharide is subject to a coupling reaction with a hydrophilic polyester or polysaccharide, or subject to a graft copolymerization process. For instance, grafting of alginic acid (which contains a carboxyl group in each repeating saccharide unit) and carrageenan (which contains sulfate groups) can be preceded by esterification with ethanol. The carboxyl and sulfonyl groups will be first converted into the appropriate acid halides by reaction with $PCl_5$, followed by reaction with ethanol under basic catalysis. Each of the esterificated polysaccharides can then be subjected to graft copolymerization at one end of the polysaccharide, e.g., with ε-caprolactone in the presence of a tin(II) octanoate catalyst. See, e.g., Choi et al., Macromolecules 1999, 32, 7402-7408; Ydens et al., Macromolecules 2000, 33, 6713-6721; and Donabedian et al., Macromolecules, 1998, 31, 1032-1039.

Ionic groups may be present in the polysaccharide before the copolymer synthesis or can also be introduced onto a hydrophilic polysaccharide after the copolymer has been synthesized. For instance, carboxymethyl polysaccharide derivatives can be prepared by carboxymethylation of a polysaccharide with chloroacetic acid in an aqueous solution containing 80% isopropanol or ethanol under basic conditions. The reaction can be carried out, e.g., at 80° C. for 1.5-2 hours. See, e.g., Oka et al., Japan Patent No. 46029504. Sulfonation can be efficiently achieved, for example, with chlorosulfonic acid in pyridine at 100° C. for 1 hour. See, e.g., Yamamoto et al., Carbohydr. Polym., 1994, 14, 53-63. The products can be thoroughly dialyzed with deionized water to remove residual reactants.

Alternatively, derivatization (e.g., carboxymethylation or sulfonation) of a hydrophilic polysaccharide can be carried out on the shells of crosslinked particles as the last step of the synthesis.

A large number of hydroxyl groups are required to impart hydrophilicity so that the amphiphilic copolymers can form micelles in a solution. Thus, if the synthesis involves protection of the hydroxyl groups, mild deprotection before micelle formation is necessary to restore the hydrophilic character of the polysaccharide chain, as well as to provide available sites for cross-linking. The hydrolysis, which can be carried out in basic conditions at room temperature, may cleave some of the polycaprolactone block, or some repeating units of the polycaprolactone block, off the polysaccharide. However, this can be advantageous for the micelle formation as shorter polycaprolactone blocks will remain, which helps assembling the block copolymers.

Additionally, the shell and or/core can be tailored to respond to environmental changes, for example, a change in temperature or change in pH. For example, N-isopropyl amide derivatives are likely to exhibit a lower critical solution temperature (LCST) below which the substance is soluble in water and above which it loses its solubility (e.g., Cho et al. Polymer 41, 5713, 2000). pH dependence of solubility is characteristic of polymers containing ionizable groups. For instance, carboxyl- or sulfonyl-containing polymers have better solubility in basic media, while polymers containing amine groups are more soluble at acidic pHs (e.g., Needham et al. Macromolecules 31, 5084, 1998).

The new amphiphilic diblock copolymers can be characterized by techniques well known in the art. For example, molecular weight can be determined by gel permeation chromatography, molecular composition can be determined by mass spectrometry, proton or carbon nucleic magnetic resonance spectrometry, or infrared spectrometry, and the viscosity can be determined by using a capillary or viscometer.

Applications of Novel Amphiphilic Linear Block Copolymers

The new amphiphilic block copolymers can be used in a variety of applications. For example, they can be used as surfactants, because of their amphiphilic nature. They can also be used as food or beverage additives in food processing, or as matrices in tissue engineering, as they are not toxic and can be biodegraded into nontoxic lower carbohydrates. They can also be used in or as coatings, emulsifiers, or compatibilizers.

Preparation of Particles of Amphiphilic Linear Block Copolymers

Figure 5:
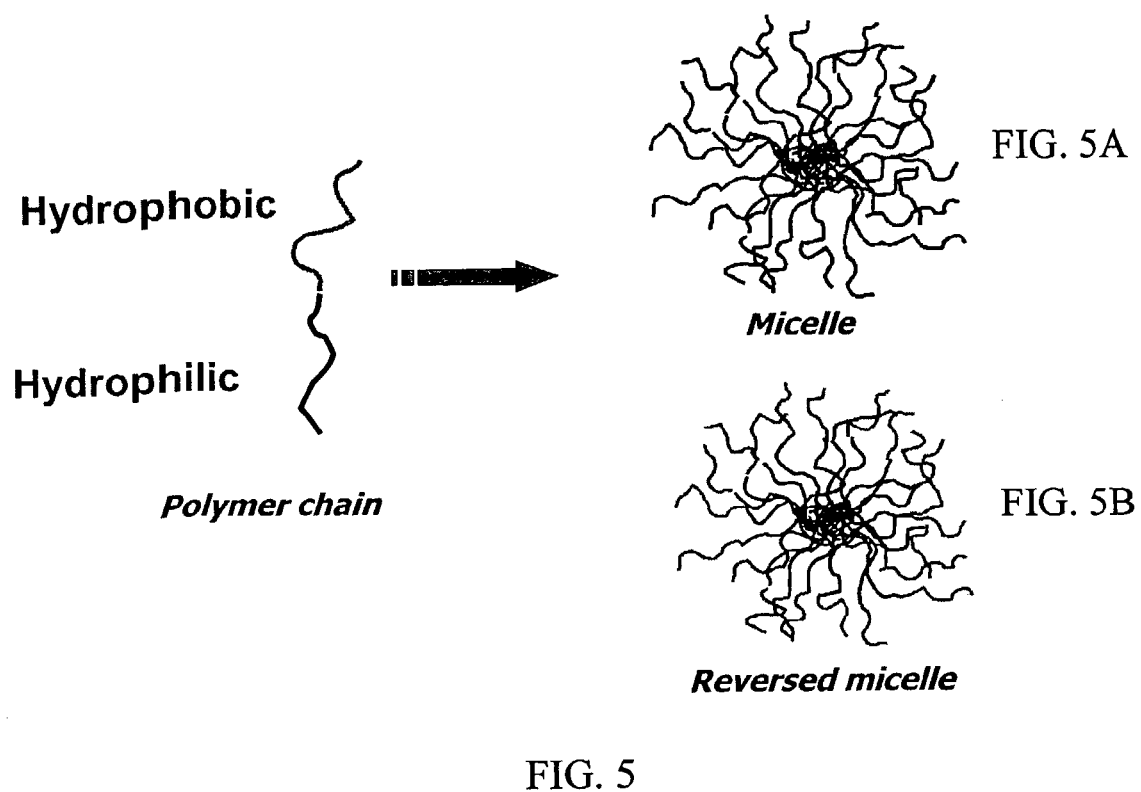
FIGS. 5A and 5B are schematics that illustrate micelle formation during synthesis of micro- and nano-particles.

Another use of the new block copolymers is to prepare particles such as micelles as illustrated in FIGS. 5A and 5B. These particles can be prepared by emulsion polymerization, self-assembly, or other known techniques for producing micro- or nanoparticles. For example, these particles (i.e., microparticles or nanoparticles) of an amphiphilic block copolymer, e.g., a diblock copolymer, can be prepared according to the following procedure.

An amphiphilic diblock copolymer is first dissolved in a solvent, e.g., N,N-dimethylformamide (DMF) or dimethyl sulfoxide (DMSO). To this solution is gradually added water or an aqueous solution or buffer (selective solvent) until micellization begins. Alternatively, micellization can be induced by slowly cooling the solution. Micelle formation may also be induced by directly dissolving the amphiphilic diblock copolymer in a solvent, such as water. Depending on the solvent, the shells of the micelles may consist of the hydrophilic or the hydrophobic block of the copolymer. Specifically, if the solvent is hydrophilic, then the shells contain hydrophilic blocks of the amphiphilic copolymer, and the hydrophobic blocks form the core, as illustrated in FIG. 5A. Likewise, to form reversed micelles having a shell of hydrophobic polymer blocks and a core of hydrophilic blocks, as illustrated in FIG. 5B, a hydrophobic solvent is required. The mixture thus obtained is stirred, e.g., for 5, 8, 10, or 15 hours, for the formation of micelles, and then dialyzed against water to remove the organic solvent, thereby stabilizing the micelles. Freeze-drying will produce solid micelles. The shells of the micelles thus obtained can then be crosslinked, e.g., with glutaraldehyde under slightly acidic conditions, or with epichlorohydrin or epoxy bifunctional ethylene glycol under slightly basic conditions, to give product particles. Polysaccharide can be crosslinked under close to neutral conditions by using a diacyl chloride such as adipoyl chloride in a nonprotic solvent such as N-methylpyrrolidone. See, e.g., Orienti et al., Arch. Pharm. Med. Chem., 2000, 333, 421-424. Different degrees of cross-linking of the particles can be obtained and tested by swelling and drug (e.g., insulin) protection studies. Adjusting the degree of cross-linking can control solubility and degradation rate of the particles. The morphology of the particles can be characterized by atomic force microscopy or scanning electron microscopy.

Figure 6:
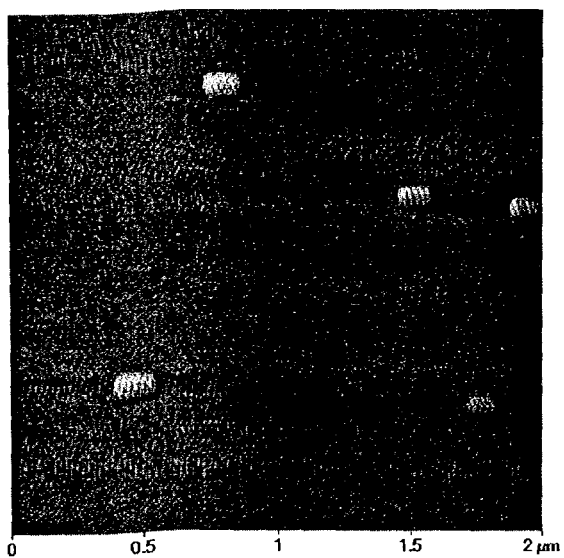
FIG. 6 is an atomic force microscopy image of cationic crosslinked hollow nanoparticles prepared from pullulan-b-polycaprolactone.
Figure 7:
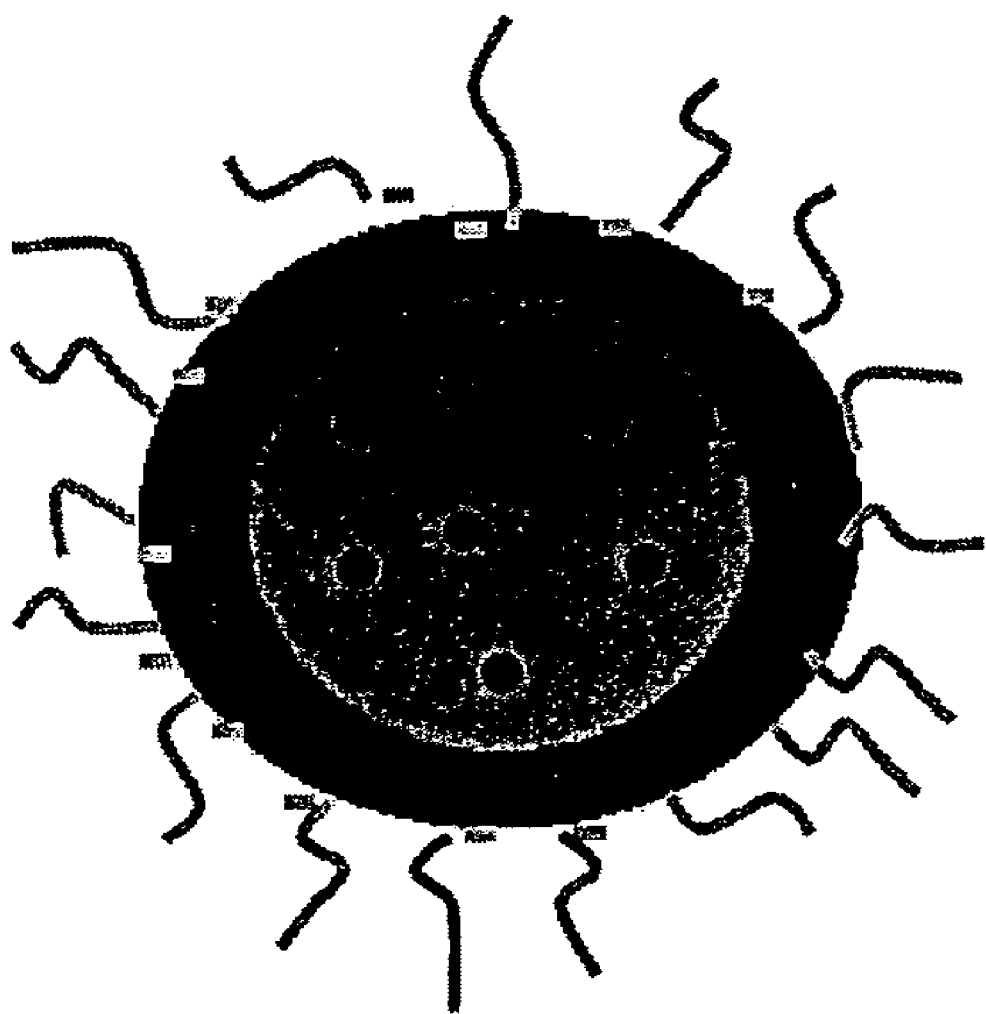
FIG. 7 is a schematic illustrating the binding of fatty acids to a cationic nanoparticle.

The particle size can be measured in either a dry or swollen state by using a microscope such as atomic force microscope or in solution using dynamic laser light scattering. Depending on the molecular weight of the copolymer, the particles can have a diameter of about 1-200 nanometers (nanoparticles) or about 200-1,000 nanometers (microparticles). FIG. 6 is an atomic force microscopy image of nanoparticles with an average diameter of 126 nm and an average height of 11.3 nm. These dimensions are for nanoparticles, which have been dried onto mica and therefore are expected to be "flattened" during this step. These sizes allow the particles to be used in various pharmaceutical compositions and applications.

Particle Core Removal

The particles of the novel amphiphilic linear block copolymers can be made hollow by removing the core, e.g., by acidic or basic hydrolysis, by ozonolysis or by enzymatic degradation of the polymer blocks forming the core. For example, a polycaprolactone core can be removed by hydrolysis under basic conditions, which gives better results than acidic hydrolysis. See, e.g., Zhang et al., J. Am. Chem. Soc., 2000, 122, 3642-3651. For instance, an aqueous mixture of the crosslinked spheres can be stirred at room temperature at about pH 12 for up to 14 days or more to hydrolyze the core. The core can also be removed by ozonolysis if the core-forming polymer contains double bonds in the main chain, e.g. polyisoprene (Wooley et al. J. Am. Chem. Soc. 121, 3805, 1999).

An agent can be introduced into the space created by removing the core. These agents can be, for example, a drug or a cell. The hollow particles can also be used with or without an added agent, e.g., to sequester an undesirable substance from a specific environment, e.g., within an animal or human subject, or in contaminated water or soil, or both. Alternatively, certain agents can be infused into the cores, and thus the cores need not be removed. In other embodiments and depending on their size, the cores of the new particles can be hollow, and thus need not be removed to create a space for containing an agent.

Thus, the core itself can be hollow or filled. The shell of each particle can be partially or fully crosslinked, before, during, or after the agent is introduced.

Loading the Particles with Agents

A variety of agents can be incorporated into the new particles. For instance, if required, the particles first can be made hollow by removing their cores, e.g., by chemical hydrolysis, ozonolysis, or by enzymatic degradation. Subsequently, the agent can be introduced into the hollow particles. Alternatively, the agent can be directly infused or perfused into the particles without removing the cores, e.g., during self-assembly of the particles. The type of agents that can be loaded into the particles include drugs, vitamins, nutraceuticals, cells, reporter groups such as radiolabeled agents, biologically active substances such as DNA, RNA, genes or active fragments, proteins, peptides, small organic and inorganic molecules, enzymes, antibiotics, vaccines, and polysaccharides. Particles loaded with nutraceuticals, such as plant sterols, can be incorporated into food substances, for example the nutraceutical-loaded particles can be dissolved into liquids such as beverages.

Generally, an agent can be incorporated into particles by first letting the particles swell in a solvent (e.g., water), and then adding the agent to the solvent so that the agent can diffuse into the cores of the swollen particles. For instance, particles of a new amphiphilic diblock copolymer containing carboxylic groups can be first incubated in a pH 8-12 aqueous solution for maximal swelling. The particles can then be added to a basic buffered saline which contains an agent, such as a drug, e.g., insulin, which is an acid-sensitive protein, so that the drug can diffuse into, thereby becoming incorporated in, the cores of the swollen particles. The mixture is then incubated for an extended period of time to achieve maximal incorporation. The pH of the incubation medium is then reduced to cause the particles to contract and to trap the drug within. Sodium phosphate can be added with acid-sensitive drugs to further protect them from acid by functioning as a buffer system. Other additives, particularly hypoglycemic agents, can also be incorporated into the particles along with insulin. Other acid-sensitive agents can also be incorporated into particles in a similar manner.

By using radiolabeled insulin, one can determine the incorporation level by counting the particles with a gamma counter.

Optionally, prior to adding the agent, the shells of the swollen particles can be partially crosslinked. After the agent has diffused into the cores of the particles, the partially crosslinked shells are then further or fully crosslinked so that the pores of the shells become smaller, making it more difficult for the incorporated agent to diffuse out of the particles.

When the shells of the particles are not crosslinked, one can incorporate a hydrophobic agent into the particles during self-assembly.

Delivery of the Particles

The agent-loaded particles can be used in a dry form or as a mixture with a solvent. Depending on their solubility, these particles can be used to deliver the agent either systemically or site-specifically. For example, when the particles carry ionic groups on the shells, they are soluble in blood and can be used for systemic delivery of an agent. When the shells of the particles contain hydrophobes, these particles become water insoluble and are suitable for site-specific delivery of an agent. These particles can also be used to form a pharmaceutical composition and can be administered via a parenteral route, e.g., topically, subcutaneously, transdermally, intraperitoneally, intramuscularly, and intravenously. The pharmaceutical composition, when prepared in an appropriate form, can also be administered nasally (e.g., as a nasal spray to form a mist), orally, rectally, vaginally, or ophthalmically.

The particles can thus be used to deliver biologically active substances such as nucleic acids, e.g., in the form of DNA vaccines, through mucosal and transdermally. In other examples, acid-sensitive agents such as insulin can be delivered orally by first loading insulin into nanoparticles containing carboxylic groups in the shell. The drug in the core is protected from acid in the stomach due to contraction of the particles under acidic conditions and is released only in the intestine, where alkaline conditions cause the particles to swell, opening up the pores and releasing the drug. Targeted delivery can thus be achieved.

Imaging and Treatment of Diseases

The particles can be labeled with a targeting agent and used as imaging or diagnostic agents by homing to targets in the body associated with a particular disorder. For example, nanoparticles can be used to image or detect malignant tumors. Cancer cells are thought to have a large number of receptors for cytokines such as interleukin 13 (IL-13). Thus, nanoparticles can be labeled with IL-13 (the targeting agent) to bind to the target receptors, and with a reporter group such as x-ray imaging agents (e.g., radio-opaque molecules), magnetic resonance imaging agents (e.g., superparamagnetic molecules such as gadolinium), or radioactive markers, and then used to image or detect cancer cells by simple systemic administration and imaging using standard in vivo imaging techniques.

Another example of a good target for imaging or detecting cancer cells is the large number of folate receptors on cancer cells. Thus, nanoparticles can be labeled with folate as a targeting agent to bind to the target receptors and then used to detect the presence of cancer cells or to image those cells.

Furthermore, bioactive nanoparticles labeled with a targeting agent can be used to treat disorders, such as cancer. For example, [99] Technetium can be incorporated into nanoparticles to make them bioactive, and when labeled with a targeting agent such as IL-13 or folate, these bioactive particles can be used to bind to and destroy cancer cells, because [99]Technetium is a chemo-therapeutic agent. Other radioactive and chemotherapeutic agents can be similarly bound to the surface or loaded into particles that are also labeled with a targeting agent that allows them to home to a particular site, such as a tumor, that is associated with a particular disorder. Other disorders and their associated targets and targeting agents are known.

Biologically Active Particles

Particles, such as nanoparticles, can be biologically active, either by the nature of their polymers or by the addition of a biologically active agent (e.g., antibacterial, antiviral, anticoagulant, anti-inflammatory, or anticancer agent).

Certain polymers that can be used in the new copolymers and particles are known to have anti-microbial activity. For example, chitosan has good biocidal properties (Blowes, P. C. et al, WO Pat. 049219A1; Begin, A. et al., *Int. J. Biol. Macromol* 1999, 26(1), 63-67; Uraki, et al., *Kichin, Kitosan, Kenkyu* 1998, 4(2), 150-151). Further, it has been shown that imparting quaternary ammonium groups with permanent cationic charge gives more effective antimicrobial agents (Kato, Y. et al., JP Pat. No. 10295785). In addition to naturally antibacterial polysaccharides, other polysaccharides can also be functionalized to obtain such properties. Generally, glycidyl trimethylammonium chloride or diethylammonium ethyl chloride can be used for the amination of carbohydrates. The former results in permanent ammonium ions while the latter can be deprotonated to give neutral amine. These reagents can also be used to increase the functionality of chitosan.

Numerous natural polysaccharides have also been shown to have antiviral activity (Premanathan, M. et al., *Antiviral Res.* 1999, 44(2), 113-122; Zhou, J. H. et al., U.S. Pat. No. 5,939,072). These are usually sulfated polysaccharides (Lee, J. et al., *Chem. Pharm. Bull.* 2001, 49(1), 108-110), mostly obtained from seaweed. Since the activity is due to the presence of the sulfate group, synthetic polysaccharides have also been rendered antiviral by introducing anionic groups (Yoshida, T. et al., *Carbohydr. Polym.* 2000, Volume Date 2001, 44(2), 141-150), and the activity can be increased by incorporating more sulfate groups. The literature describes studies of antiviral activity mainly on HIV virus (Suzuki, F. et al., U.S. Pat. No. 6,020,325; Baba, M. et al., *Proc. Natl. Acad. Sci. U.S.A.* 1988, 85(16), 6132-6; Hashimoto, K. et al., *Antiviral Chem. Chemother.*, 1996, 7(4), 189-196), but also on herpes simplex and a more limited number of tests have been done on less common types of enveloped viruses, such as rubella, influenza A and B, respiratory syncytial virus, measles, human cytomegalovirus, Junin and Tacaribe virus, simian immunodeficiency virus, rabies, African swine fever, etc.

The exact mechanism of action is unknown. However, numerous tests indicate that sulfated polysaccharides inhibit the adhesion of virus to cells and the early steps of virus replication, such as internalization and uncoating. The inhibitory function depends on the charge density and the shape of the molecule, but is independent of the sugar repeating units. In fact, sulfated synthetic polymers have also given positive tests. While the inhibition described above is general, regardless of the structure of the polysaccharide, infection initiated by transfection of cells with viral RNA is affected only by certain sulfated polysaccharides, and the efficiency varies with the virus strain. For the above reasons, the sulfated polysaccharide must be present before virus adhesion.

Sulfated polysaccharides show other beneficial biological properties as well. They include anticoagulant, antithrombotic (Alban, S. et al., in book titled, "Carbohydrates in drug design", Marcel Dekker, New York, pp. 209-276, 1997), anti-inflammatory (Arfors, K.-E. et al., *J. Lab. Clin. Med.* 1993, 121, 201-202), anti-adhesive (Ley, K. et al., "*Am. J. Physiol* 1991, 260, H1667-H1673), antiproliferative, antiatherosclerotic, antiangiogenetic, antimetastatic, and complement-inhibiting activities (Engelberg, H. et al., *Seminars in Thrombosis and Hemostasis* 1991, 17, 5-8). In addition, sulfated polysaccharides are known to decrease blood cholesterol levels via inhibiting pancreatic cholesterol esterase (Lange, III. et al., U.S. Pat. No. 5,063,210). Thus, all of these activities can be created in the new copolymers and particles by using any one or more of these biologically active polymers in the preparation of the new copolymers and particles.

Sequestering of Substances

Particles of a new amphiphilic diblock copolymer can also be used to remove undesirable substances from the fluids in the body or from the environment or from a contained liquid. This can be done by binding agents onto the surface of the particles, so that these agents can interact with the undesirable substance and remove it from the fluid. The sequestered substance can then be transferred into the cores of the particles. For example, cationic nanoparticles exhibit selective interaction with bile acids. Thus, the positively charged cationic nanoparticles will bind and thus remove negatively charged bile acids from the entero-hepatic circulation and excrete them into the feces. This is represented schematically in FIG. 9.

In another example individuals with chronic renal failure often suffer from hyperphosphatemia as a result of the inability of kidneys to excrete excess phosphate. Cationic nanospheres can bind the negatively charged phosphate ions and reduce the hyperphosphatemia. Other examples of substances that can be removed using nanoparticles include bile acids, toxins, metal ions, and complex ions (e.g., phosphates). Because crosslinking prevents particles from disintegrating, particles having crosslinked shells are more stable. Thus, crosslinked particles are safer and more effective in removing undesirable substances from a body or environment and trapping them. In addition, particles having ionic groups on the shells are more effective at attracting and trapping charged substances than particles having no charges on the shells. Further, the larger the surface areas of these particles, the more efficient they are in removing and trapping undesirable substances. For example, bile acids (anionic materials) bind to cationic nanoparticles and are trapped inside the cationic nanoparticles. In addition, one could make cationic or anionically charged nanoparticles for chromatographic applications that can be used to separate, identify, quantitate, or extract negatively or positively charged products, respectively, of synthetic reactions.

Specifically, the low pH (acidic) environment of the stomach facilitates swelling of particles in which the shells are crosslinked. The swelling increases the size of the pores on the surface of the particles, allowing agents, for example bile acids, to enter the particles through the enlarged pores on the surface and diffuse into the cores of the particles. When the particles travel to the small intestine, which has an alkaline environment (high pH), the pores on the surface of the particles contract in size, thus preventing release of the agents, and traps the agents in the core of the particles. Thus, excess bile acids can be removed from enterohepatic circulation.

The sequestering efficacy of specific particles of the new amphiphilic diblock copolymers can be preliminarily determined in vitro or in vivo by methods well known in the art.

Appropriate in vitro studies can be used to reasonably predict the in vivo results of the efficacy of the particles in capturing a substance.

The invention is further described in the following examples, which are only illustrative and do not in any way limit the scope of the invention described in the claims.

EXAMPLES

Example 1

Hydrolysis of Pullulan 300 g pullulan (Pfanstiehl Laboratories, Inc., average molecular weight 200,000) was dissolved in 3 L of water. 6 mL of concentrated hydrochloric acid was added to obtain a 0.02 M solution. The solution was stirred at 60° C. for 4 days. The product was precipitated with methanol and dried under vacuum. The recovered 257 g pullulan was dissolved in 2600 mL water and heated to 60° C. To the aqueous solution thus obtained, 5.2 mL of concentrated hydrochloric acid was added and the solution was stirred at 60° C. for 4 days. After it cooled to room temperature, the product was precipitated with methanol and dried under vacuum to give 181.07 g pullulan ($M_n$=4700, $M_w$=6500).

Example 2

Hydrolysis of Pullulan

Pullulan (300 g, TCI America, MW~200,000) was dissolved in 3 L of distilled water and heated to 60° C. and a concentrated solution of hydrochloric acid (6.0 ml) to obtain a 0.02 M solution. The solution was stirred at 60° C. After the desired reaction time (as specified in Table 1), the solution was poured into 1 gallon of methanol. The white precipitate was separated by filtration, washed with methanol and dried in vacuum overnight. The molecular weights measured with gel permeation chromatography are listed in Table 1. In table 1, $M_n$ refers to the number average MW, $M_w$=weight average MW, $M_z$ is the z average MW, $M_p$ is the p average MW, and MWD is the molecular weight distribution.

TABLE 1

Molecular weights of hydrolyzed pullulan

| Time, days | $M_n$ | $M_w$ | $M_z$ | $M_p$ | MWD |
|---|---|---|---|---|---|
| 2 | 12620 | 24010 | 38660 | 20633 | 1.90 |
| 4 | 7338 | 12835 | 19582 | 11851 | 1.75 |
| 6 | 6015 | 9785 | 14422 | 9615 | 1.63 |

Example 3

Synthesis of a Pullulan-Co-Polycaprolactone 1 gram of pullulan obtained from Example 1 ($M_n$=4700, $M_w$=6500) was dissolved in 20 ml of N,N-dimethylforamide (DMF) by heating the mixture until complete dissolution. To the DMF solution was added sodium hydride obtained from 1.2 g 60% dispersion in mineral oil by washing the dispersion with tetrahydrofuran (THF). The mixture was heated at 80° C. for 2 hours under argon gas and subsequently cooled in an ice bath. To this mixture, 3 mL of chloroacetyl chloride was then added dropwise. The resultant mixture was heated at 80° C. for 2 hours and cooled to room temperature again, and then poured into ice water to give a first precipitate. The first precipitate was washed with water and dried under vacuum. Alternatively, 5.0 g of pullulan obtained from Example 1 was dissolved in 75 mL of N,N-dimethyl acetamide (DMA) by heating the mixture until complete dissolution. To this solution there was added sodium hydride obtained from 6.0 g 60% dispersion in mineral oil by washing the dispersion with THF. The mixture thus obtained was stirred at room temperature for 4 hours before it was cooled in an ice bath and 15.0 mL chloroacetyl chloride was added dropwise. The resultant mixture was stirred at room temperature for 4 hours and subsequently poured into ice-cold water to give a first precipitate. The first precipitate was washed with water and dried under vacuum.

2 grams of the first precipitate was mixed with 4 ml of a 30% solution of HBr in glacial acetic acid. The mixture was stirred at room temperature for 1 hour and poured into ice water to give a second precipitate. The second precipitate was washed with water and dried in a vacuum.

4.5 grams of a polycaprolactone (average m.w. ca. 10,000, Aldrich, Milwaukee, Wis.) was dissolved in 20 ml of dry THF. 20 grams of drierite and 116 mg of silver oxide were added to the polycaprolactone solution and stirred for 1 hour at room temperature. 26 mg of iodine was then added to the mixture. To this mixture, a solution of 2 grams of the second precipitate in 6 ml of dry THF was added dropwise. This mixture was stirred at room temperature for 24 hours while it was protected from light. The resultant mixture was filtered on a glass filter and the solvent was removed under reduced pressure to give the diblock chloroacetopullulan-co-polycaprolactone. The amphiphilic diblock pullulan-co-polycaprolactone was obtained by mixing the product with 100 ml methanol and stirring it with 18.7 ml aqueous 0.82 M sodium hydroxide solution for 1 hour. The product was filtered and dried.

Example 4

Synthesis of a Pullulan-Co-Polycaprolactone

A 3-neck flask was charged with 9.0 grams chloroacetic acid and 144 ml trifluoroacetic anhydride and heated to reflux. Hydrolyzed pullulan (30.0 grams) was added portionwise. The mixture was refluxed for 8 hours, then allowed to cool and poured into ice-cold water, neutralized with a saturated solution of sodium bicarbonate. The first precipitate, (chloroacetopullulan), was washed with cold water and freeze-dried.

The first precipitate (10.0 grams), (chloroacetopullulan), was dissolved in 10.0 ml glacial acetic acid and stirred with 5.0 ml 30% solution of hydrogen bromide in acetic acid for 20 minutes. The second precipitate, (chloroacetobromopullulan), was precipitated with ice-cold water, washed with water, and freeze-dried.

A 3-neck flask equipped with a mechanical stirrer was charged with 40.0 grams polycaprolactone (MW~2,000), 30 grams Drierite, 0.555 grams silver (I) oxide, 0.235 grams silver (I) carbonate and 120 ml freshly distilled dry methylene chloride. The mixture was protected from light and stirred for 1 hour, then 0.252 grams iodine was added. A solution of 20.0 grams of the second precipitate, (chloroacetobromopullulan), in 50.0 ml freshly distilled dry acetone. The mixture was stirred for 10 days under argon. The product was filtered on course filter paper, then on glass fiber with the aid of tetrahydrofuran. The solvent was evaporated under vacuum. The third precipitate, (chloroacetopullulan-co-polycaprolactone), was deprotected by first dispersing it in 200 ml methanol, then adding a mixture of 800 ml methanol and 26 ml cc.

ammonium hydroxide solution and stirring the mixture for 10 minutes. The fourth precipitate was then filtered, and the deprotection was repeated. The product, (pullulan-co-polycaprolactone), was filtered and dried in vacuum, and then Soxhlete extracted with toluene for 2 days.

Example 5

Synthesis of Pullulan Glycosylamine

Hydrolyzed pullulan (2.0 grams) was dissolved in 100 ml distilled water and the solution was saturated with ammonium hydrogen carbonate. The solution was kept saturated by maintaining the presence of solid ammonium hydrogen carbonate and stirred at room temperature for 6 days. The product was freeze-dried and dissolved in a small amount of water several times, and finally freeze-dried. The percentage glycosyl amine functionality ($F_n$) was determined by $^1$H NMR spectroscopy to be $F_n$=94.3%.

Example 6

Synthesis of Polycaprolactone 4-Nitrophenyl Carbonate

Polycaprolactone (20.0 grams, Aldrich, MW~2000) was dissolved in 80.0 ml N-methylpyrolidone. 4-(Dimethylamino)-pyridine (800 mg) was added and allowed to dissolve. Pyridine (20.0 ml) and 12.0 4-nitrophenyl chloroformate were added and the mixture was stirred for 24 hours. The solution was poured into cold methanol, centrifuged, decanted, washed with methanol several times, and dried in vacuum. The percentage chain end functionality ($F_n$) was determined by $^1$H NMR spectroscopy to be $F_n$=100%.

Example 7

Synthesis of Pullulan-Co-Polycaprolactone

Pullulan glycosylamine (0.50 grams, Mn=6379) was dissolved in 5.00 ml N-methyl pyrrolidone. 4-(Dimethylamino)-pyridine (10 mg) was added, followed by 0.50 grams polycaprolactone 4-nitrophenyl carbonate (MW~2000). The mixture was stirred for 24 hours, then precipitated with cold diethyl ether. The precipitate was washed with diethyl ether and dried in vacuum. The product was extracted with toluene by stirring it in 20 ml toluene for 24 hours, then centrifuging, decanting and washing 3 times with toluene. The product was dried in vacuum. The composition of the product was determined by $^1$H NMR spectroscopy to have a polycaprolactone content of 16% by weight (52 mol %).

Example 8

Synthesis of Pullulan-Co-Polycaprolactone

Pullulan (4.0 grams, Mn=18,800, Mw=31,400) was swollen in 20 ml N-methyl pyrrolidone. 4-(Dimethylamino)pyridine (DMAP, 411 mg) was added and the mixture was stirred until all of the DMAP dissolved. The mixture was briefly heated to dissolve the pullulan, and then allowed to cool. Polycaprolactone 4-nitrophenyl carbonate (3.0 grams, 58% of the chain ends functionalized, MW~2000) was added and the mixture was stirred for 48 hours. The product was poured into 100 ml anhydrous denatured ethanol. The precipitate was filtered, washed thoroughly with anhydrous denatured ethanol and dried in vacuum. It was then extracted with toluene by stirring it in 100 ml toluene for 24 hours. The mixture was centrifuged and the solid was washed with toluene three times, then dried in vacuum. The extraction was repeated for 3 hours, followed by centrifuging and washing three times. The product was dried in vacuum. The polycaprolactone content, determined by $^1$H NMR spectroscopy, was 9.6 wt %.

Example 9

Preparation of Particles of Polysaccharide-Co-Polycaprolactone

Figure 8:
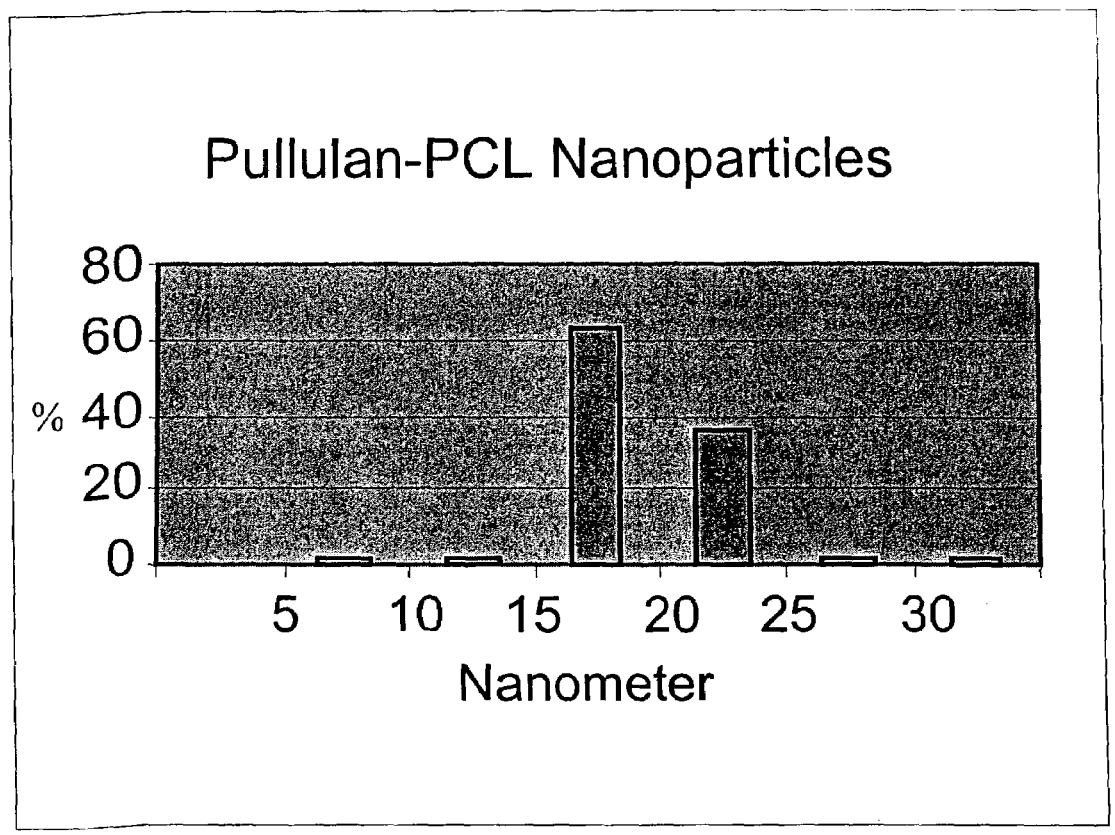
FIG. 8 is a bar graph showing the size distribution of nanoparticles of pullulan-polycaprolactone copolymer.

The diblock polysaccharide (Pullulan)-co-polycaprolactone obtained from Example 3 was dissolved in DMSO and the solution was allowed to cool slowly. The product was dialyzed in distilled water and freeze-dried to obtained particles of the copolymer. The protocol followed is as described in Example 3. As illustrated in FIG. 8, about 63% of the particles in the swollen state were in the size range of about 15 to 20 nm, and about 38% of the particles in the swollen state were in the 20 to 25 nm range. Very few nanoparticles were outside of this range, showing the specificity of size ranges that can be achieved using the methods described herein. The size and uniformity of the nanoparticles varies as the molecular weight and uniformity of the block copolymer, respectively, used to prepare the nanoparticles.

Example 10

Preparation of Particles of Pullulan-Co-Polycaprolactone

The Pullulan-co-polycaprolactone block copolymer (50 mg) obtained from Example 3 was dissolved in 2.0 ml DMSO. The solution was stirred overnight. Distilled water (10 ml) was added dropwise, then the solution was dialyzed. This results in particles of size less than ~100 nm.

Example 11

In Vitro Study of Insulin Release

Particles containing radiolabeled insulin, i.e., $^{125}$I-insulin, are incubated in an acidic solution (e.g., pH 1.5) that mimics the environment of the stomach. The radioactivity is detected in the particles and in the incubation medium at different time points by centrifuging the solution containing the particles and counting the packed fraction at the bottom of the tube (the particles) and the supernatant, to determine whether and how much of the radiolabeled insulin remains in the particles following treatment with the acidic solution.

The same experiment is carried out in a pH 10.0 solution, which mimics the environment of the small intestine where absorption of insulin into the blood stream occurs. At pH 10.0, particles containing radiolabeled insulin swell, thereby increasing their pore size and releasing the radiolabeled insulin into the medium. The amount of insulin released from the particles is determined by centrifuging the incubation medium and measuring the radioactivity of the particles and the supernatant at different time points after introduction into the alkaline solution.

Example 12

In Vivo Study of Insulin Release

Cationic and anionic nanoparticle preparations of insulin were performed as follows: 2 mL of crosslinked hollow nanoparticle solution was incubated for 24 hours with 25 mg of insulin. The preparation was dialyzed and the final insulin concentration was calculated to be 9.7 μg/mL. One animal was used for each experiment. Before the administration of insulin as a nanoparticle preparation, a regular glucose tolerance test was performed and the glucose and insulin levels were measured. This measurement was repeated after the delivery of insulin loaded in nanoparticles. Before application of the nanoparticle preparations, each animal was given a straight glucose tolerance test (GTT). For this test, animals were fasted at least 18 hours beforehand, and gavaged with 0.4 grams of glucose. Blood samples were taken at time points 10 minutes, 30 minutes, 60 minutes, and 2 hours. Prior to the applications of nanoparticle preparations, animals were fasted for at least 18 hours before the experiment. Animals were shaved to expose the skin of the back, gavaged with 0.4 grams of glucose and then the appropriate nanoparticle preparations of insulin were applied to the exposed skin.

Figure 16:
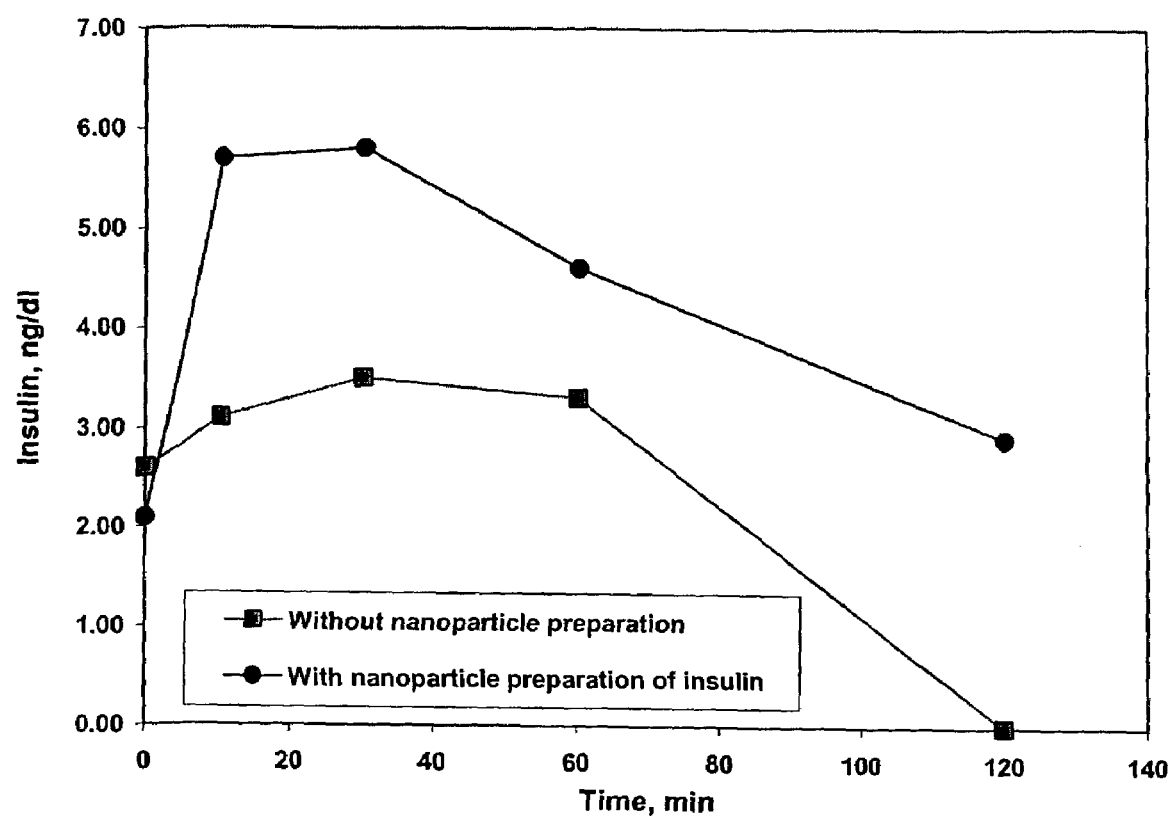
FIG. 16 is a graph that shows the glucose response of rats following topical application of insulin in conventional form and as a cationic nanoparticle preparation.
Figure 17:
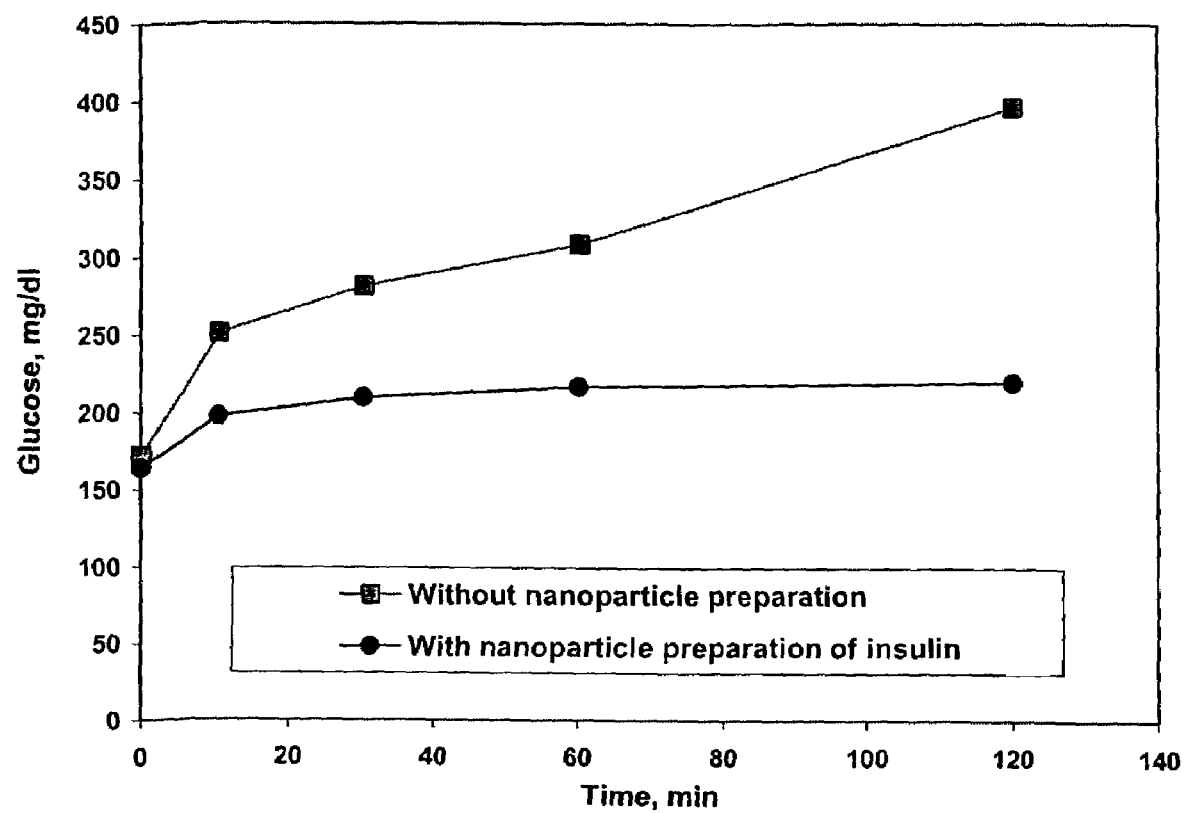
FIG. 17 is a graph that shows the glucose response of rats following topical application of insulin in conventional form and as an anionic nanoparticle preparation.
Figure 18:
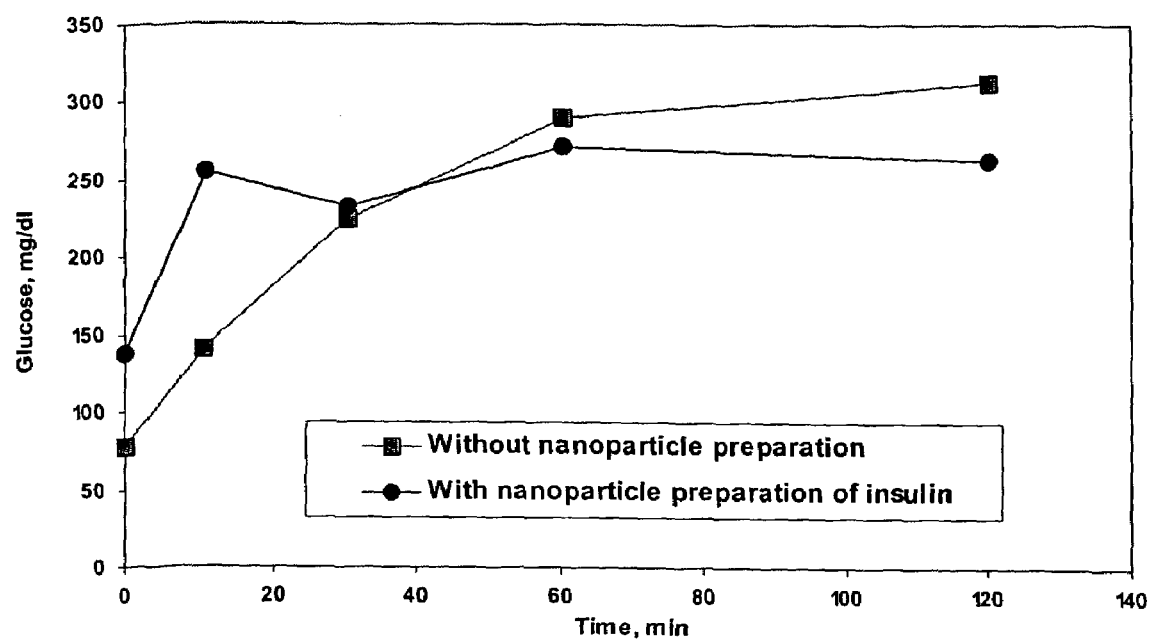
FIG. 18 is a graph that shows the insulin response of rats following topical application of insulin in conventional form and as an anionic nanoparticle preparation.

FIG. 16 shows the insulin response of rats following topical application of anionic nanoparticle preparation of insulin relative to no exogenous application of insulin. The "without nanoparticle preparation" curve reflects the insulin level in the blood, produced by the secretion of insulin in response to the initial dose of glucose received by the rat. The plot indicates a higher level of insulin in blood when a nanoparticle preparation of insulin is applied. This would lead to lower glucose levels in the blood as seen in FIGS. 17 and 18. For FIGS. 17 and 18, blood samples were taken at 5 minutes, 30 minutes, 60 minutes, and 2 hours. FIGS. 17 and 18 show plots of blood glucose concentration with time using cationic and anionic nanoparticle preparations of insulin, respectively, relative to inherent insulin secretion of the animal in response to the initial dose of glucose that animal received. As seen from the plots, blood glucose levels are lower, and are more stable (i.e., vary less with time), when insulin is administered as a nanoparticle preparation relative to its inherent glucose response.

Example 13

In Vivo Study of Treating Diabetes with Particles Containing Insulin

The streptozoticin mouse model of diabetes is used in an in vivo study of the efficacy of particles of a new amphiphilic diblock copolymer in delivering an incorporated agent.

Specifically, after diabetes has been demonstrated by measurements of glucose tolerance in the mice, particles containing a radiolabeled insulin, i.e., $^{125}$I-insulin, along with 25 mg cold insulin, were added to either the drinking water or the diet for the animals for 4 weeks. The blood glucose and insulin levels are measured at 2 and 4 weeks, and are compared to those observed in animals in which non-insulin containing particles are added to the drinking water or the diet.

Example 14

In vitro Study of Sequestering Ability of New Particles

Figure 9:
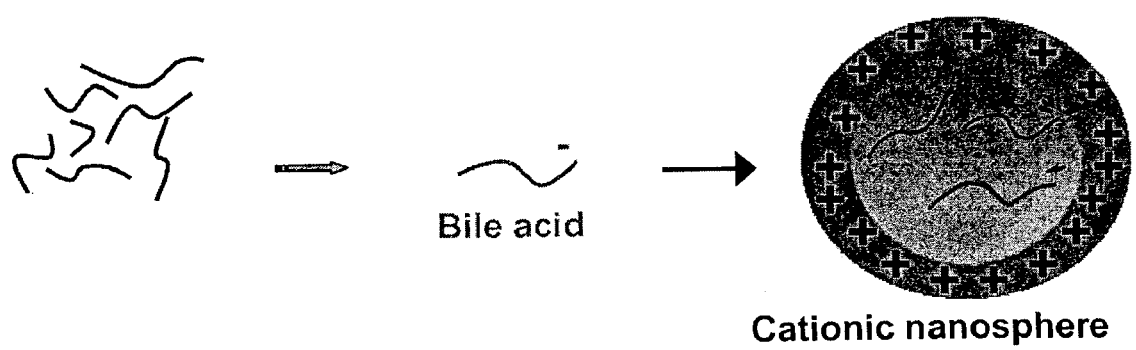
FIG. 9 is a schematic showing a cationic nanoparticle sequestering bile acids.

FIG. 9 is a schematic showing cationic nanoparticles sequestering bile acids. A bile acid solution containing the sodium salt of "cold" cholate is prepared in a simulated colonic solution of NaCl and $Na_2CO_3$ and adjusted to pH 6.8 with HCl. The sodium salt of "cold" cholic acid is mixed with carboxyl-$^{14}$C radiolabeled cholic acid and an aliquot of this working solution is then added to 5 mg of particles of an amphiphilic diblock copolymer. The mixture is incubated in a shaking water bath at 37° C. for an extended period of time with the pH value maintained at 6.8. The mixture is filtered through Whatman #2 and the filtrate is taken for determination of its radioactivity. Alternatively, the mixture is centrifuged, and an aliquot of the supernatant can be removed from the top and placed into a scintillation vial. After the addition of 5 ml scintillation fluid, the solution is allowed to stand overnight. Finally, the vial is placed in a scintillation counter and radio counts are recorded.

Example 15

In Vivo Study of Sequestering Ability of New Particles

An in vivo study in hamsters is conducted to determine the efficacy of the new particles of the new amphiphilic diblock copolymers in sequestering bile acid from a body according to a binding assay described in Kowala et al., Atherosclerosis, 1991, 91, 35-49; Wilson et al., Metabolism, 1998, 47, 959-964; and Wilson et al., Atherosclerosis, 1998, 140, 315-324

Example 16

Encapsulation of α-Tocopherol

α-Tocopherol (50 mg) was dissolved in 4.0 ml of methyl sulfoxide. Pullulan-co-polycaprolactone block copolymer (100 mg) was added. The mixture was heated in a microwave oven at 260 W for 35 seconds, then stirred at room temperature overnight. The solution was filtered using a 0.45μ syringe filter. Distilled water (10 ml) was added dropwise and the solution was dialyzed. A slightly cloudy solution was obtained (20 ml), which had a measured α-tocopherol content of 1 mg/ml.

The following experiments were done to demonstrate uptake of tocopherol when delivered transdermally using pullulan nanoparticles.

One hamster was isolated and fasted overnight; a fasting blood sample was collected. Two days later, another fasting blood sample was collected. Plasma was isolated from these 2 samples for the measurement of baseline levels of tocopherol. Two days after the second baseline fasted blood sample was collected, the animal was fasted again, and the skin on the back was exposed. 1 mL of a nanoparticle preparation of tocopherol, prepared as described above was applied topically to the skin at the back of the animal. This sample was previously analyzed to contain 910 μg/mL of tocopherol. Blood samples were collected at 1, 3, 5, 22, 44, and 95 hours after topical application. Plasma was extracted from each sample, and analyzed for vitamin E quantity using a HPLC system. Sample concentrations were calculated by comparison to a standard sample of known concentration of tocopherol.

Figure 10:
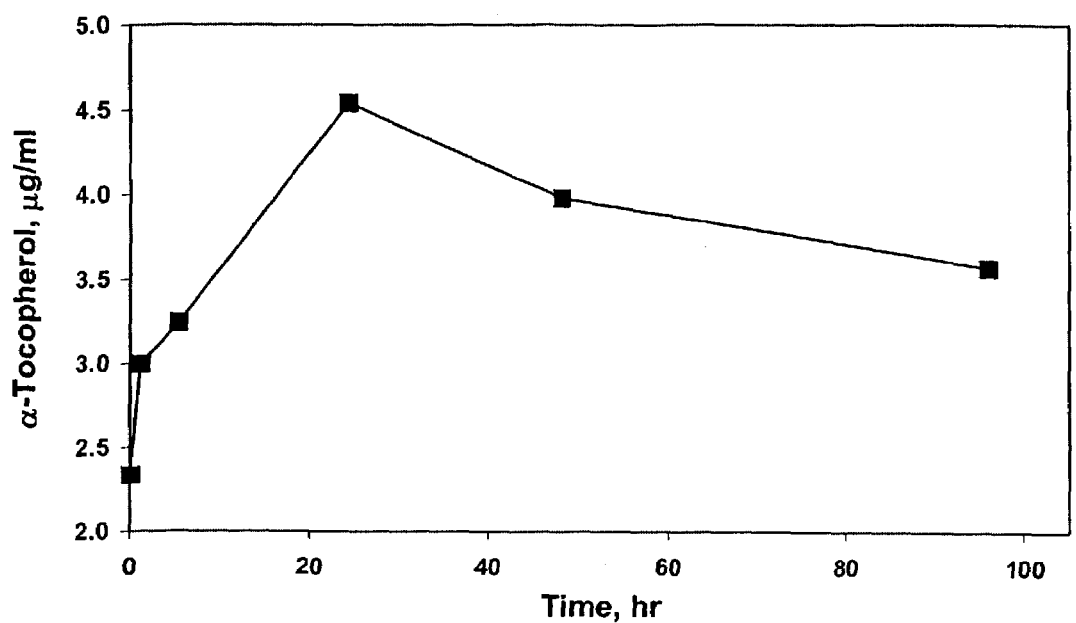
FIG. 10 is a plot of α-tocopherol levels in the blood (of hamster) following topical application of a nanoparticle preparation containing α-tocopherol over time.

FIG. 10 gives a time plot of the amount of tocopherol in the blood following topical delivery of tocopherol using nanoparticles. As can be seen from the plot, topical administration of tocopherol using nanoparticles results in a high bioavailability in blood of the tocopherol. This represents a very high enrichment in the blood of tocopherol after just one-5 minute administration of tocopherol topically. In addition, tocopherol being fat soluble can only be delivered in an oil mixture until now. Now you can deliver tocopherol in a water base by using our nanoparticles. The ability to deliver these nanospheres in water orally will be a major breakthrough as this cannot be done now except as a large micelle which cannot be used in water because of its cloudy nature.

Example 17

Encapsulation and Anti-Inflammation Studies of Celebrex®

Figure 11:
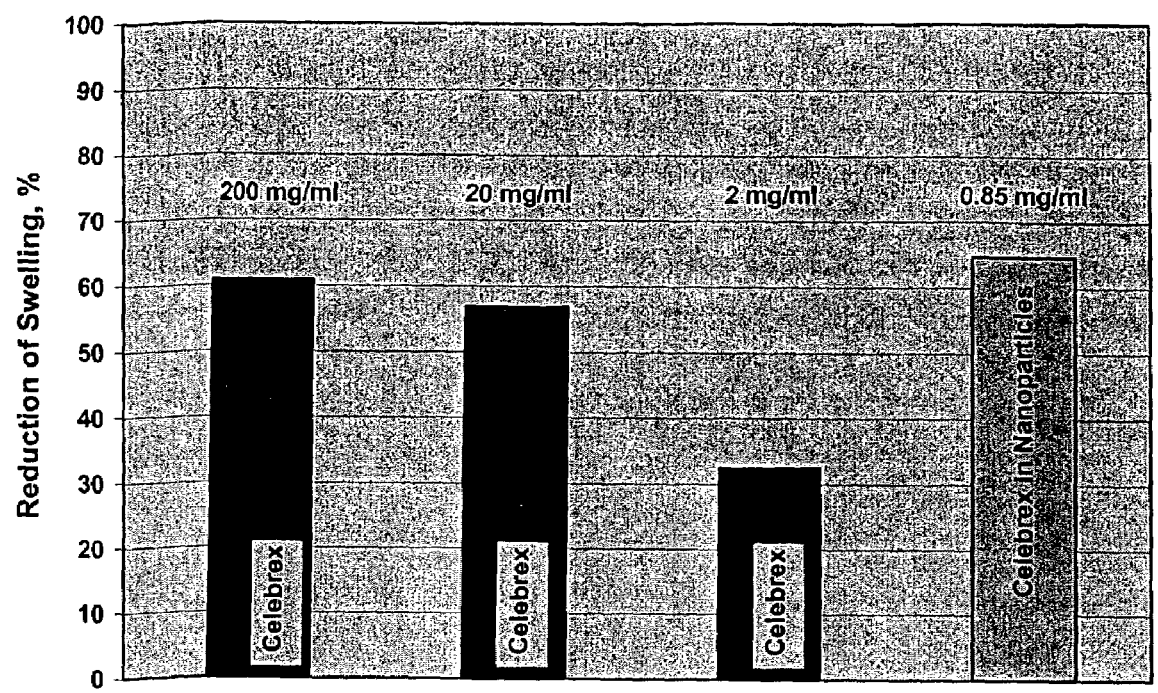
FIG. 11 is a dose-response study of topical administration of Celebrex® as an anti-inflammatory agent and its nanoparticle preparation. The values above the bars indicate the concentration of Celebrex in the solution.

Pullulan-co-polycaprolactone (200 mg) was mixed with 100 mg Celebrex® (celecoxib, is chemically designated as 4-[5-(4-methylphenyl)-3-(trifluoromethyl)-1H-pyrazol-1-yl]) benzenesulfonamide and the mixture was dissolved in 2.0 ml methyl sulfoxide. The mixture was stirred with dropwise addition of 10 ml distilled water. The solution was dialyzed in a regenerated cellulose dialysis tube having a molecular weight cut-off between 6000-8000 daltons. After dialysis, the solution was filtered. The solution contained 22.58 µg/ml of Celebrex® as measured by UV spectroscopy Croton oil was applied to the left and right ears of five animals to cause inflammation. Two hours later, a nanoparticle preparation of Celebrex or conventional form of Celebrex® was applied topically to the left or right ear. After 6 hours of exposure (FIG. 11) shows that Celebrex® in nanoparticle form, at a dosage of 0.85 mg/ml causes a greater reduction in ear swelling (65%) than a 200 mg dose (60%), of Celebrex® delivered in conventional form, the highest dosage of Celebrex® used in this experiment. Thus, Celebrex® in nanoparticle form is significantly more effective as a topical anti-inflammatory at significantly lower doses.

Example 18

Encapsulation of Acetylsalicylic Acid

Pullulan-co-polycaprolactone (200 mg) was mixed with 100 mg acetylsalicylic acid and the mixture dissolved in 2.0 ml methyl sulfoxide. The mixture was stirred with dropwise addition of 10 ml of distilled water. The solution was dialyzed in a regenerated cellulose dialysis tube having a molecular weight cut off between 6000-8000 daltons. After dialysis, the solution was filtered. The solution contained 23.27 µg/ml of acetylsalicylic acid as measured by UV spectroscopy.

Example 19

Encapsulation of Estradiol

Pullulan-co-polycaprolactone block copolymer (100 mg) was mixed with 20 mg estradiol and dissolved in 1 ml of hot methyl sulfoxide. The mixture was filtered using a 0.45 µL syringe filter. The solution was cooled to room temperature and 5 ml water was added dropwise. The mixture was stirred overnight, then dialyzed in a regenerated cellulose dialysis tube having a molecular weight cut off between 6000-8000 daltons. The solution was filtered using a 0.45 µL syringe filter. The encapsulated estradiol concentration was determined to be 4200 pg/ml.

Pullulan-co-polycaprolactone block copolymer nanoparticles encapsulated with estradiol were calculated to contain 57 µg/ml of estradiol while the micelle preparation, was calculated to contain 88 µg/ml of estradiol.

Figure 12:
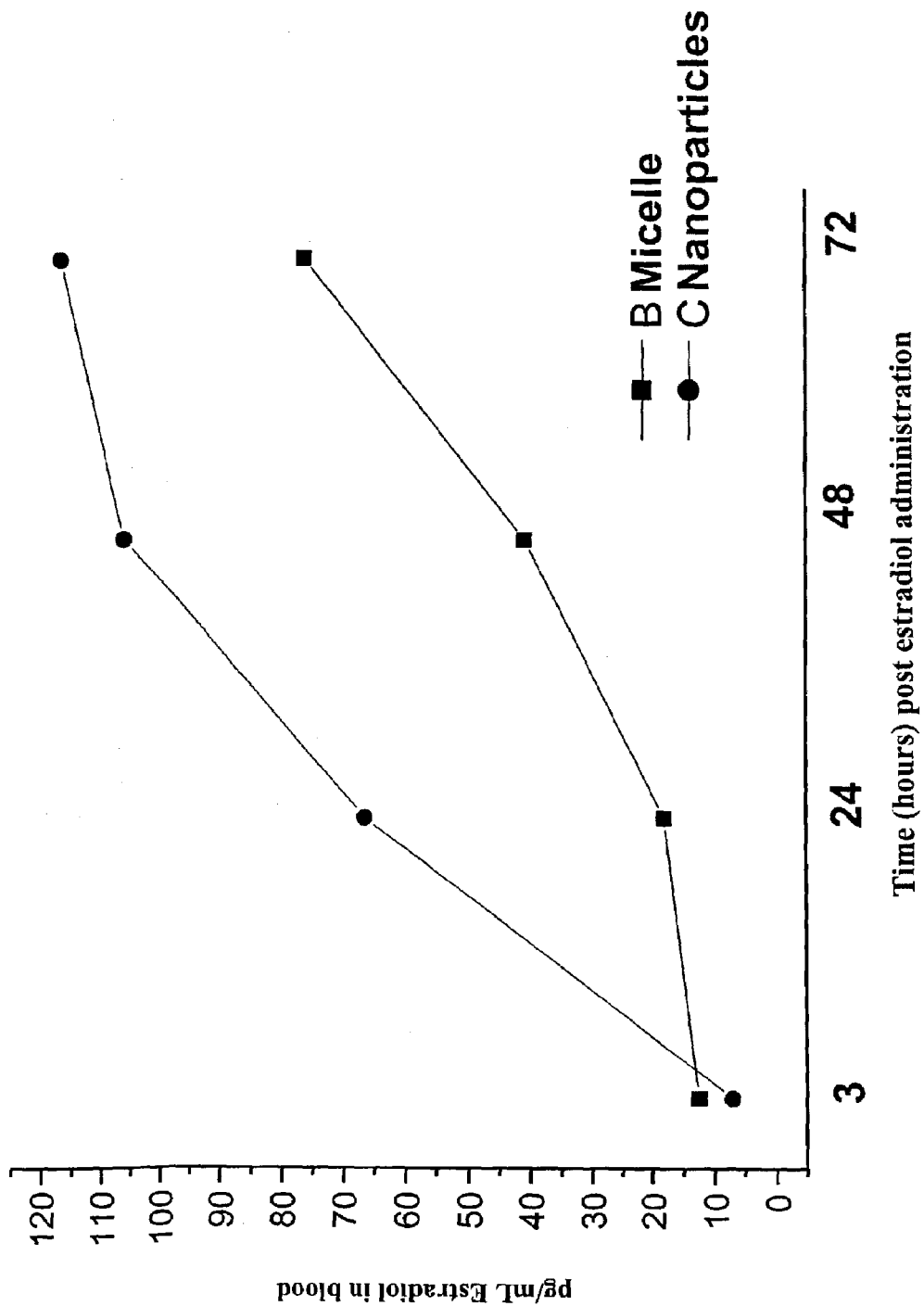
FIG. 12 is a plot of estradiol levels in the blood (of hamster) following oral delivery of micelle and nanoparticle preparation containing estradiol over time.

Blood samples were obtained from each hamster prior to treatment application, for baseline estradiol concentrations. Hamsters receiving oral applications were gavaged with 1 mL of the appropriate preparations. Blood samples were centrifuged in order to obtain plasma. Each plasma sample was analyzed using a Coat-A-Count Estradiol Assay kit. Concentration of estradiol in each plasma sample was calculated based on a standard estradiol concentration curve, which was obtained using calibrators included in the kit. Blood samples were obtained at 3, 24, 48, and 72 hours after oral delivery. Results are shown in FIG. 12. Oral delivery of estradiol as nanoparticle preparations yields a higher bioavailability (120 pg/mL) in blood than when delivered by micelles (75 pg/mL).

Example 20

Synthesis of Shell-Crosslinked Hollow Nanoparticles

Pullulan-co-polycaprolactone block copolymer (2.14 grams) was dissolved in 5.0 ml methyl sulfoxide. The solution was stirred for 2 hours. Distilled water (80 ml) was added dropwise, then the solution was dialyzed. To the thus obtained solution (121 ml), 388 µl epichlorohydrin was added, followed by 121 ml 6 M sodium hydroxide solution. The mixture was stirred for 24 hours. The solution was acidified to pH-6.5 with 10 M hydrochloric acid. The solution was then dialyzed. The diameter of the resultant nanospheres as measured by TEM was approximately 60 nm.

Example 21

Synthesis of Cationic Nanoparticles 2-(Diethylamino)ethyl chloride hydrochloride (0.4 grams) was mixed with 0.5 ml of a 50% sodium hydroxide solution. The mixture was allowed to stand for 10 min, then 50 ml of a 1 mg/ml solution of crosslinked hollow nanoparticles was added. The mixture was stirred at 70° C. for 2 hours. The solution was then dialyzed using regenerated cellulose dialysis tube of molecular weight cut off of 6000-8000 daltons. The degree of substitution was 0.146 (The average number of hydroxyl groups substituted per repeating unit was 0.146) as measured by $^1$H nuclear magnetic resonance spectroscopy.

Example 22

Synthesis of Anionic Nanoparticles

Chloroacetic acid (1.134 grams) was mixed with 2.0 ml of a 50% solution of sodium hydroxide and the mixture was allowed to stand for 10 min. A 4 mg/ml solution of crosslinked hollow nanoparticles (12.5 ml) was added and the mixture was stirred at 70° C. for 12 hours. The mixture was dialyzed in regenerated cellulose dialysis tube of MWCO=6-8000. The degree of substitution was measured by $^1$H nuclear magnetic resonance spectroscopy to be 0.48 (The average number of hydroxyl groups substituted per repeating unit was 0.48).

Example 23

Oral Delivery of Radiolabeled Cholesterol

A stock solution of tritiated cholesterol was counted and concluded to contain 800,000 CPM in 10 µL. A volume of 10 µL of $^3$H cholesterol was incubated with 1 mL of crosslinked hollow nanoparticles, and left to dialyze overnight, at room temperature, in a shaker. The nanoparticle preparation was dialyzed for 12 hours, and counted after dialysis. 50 µL of the nanoparticle preparation contained 2300 CPM. A saline preparation of 3H cholesterol was made using 5 µL of stock cholesterol solution and 3 mL of saline. 50 µL of this solution was counted, and contained 2800 CPM. Two rats were isolated for this experiment; one gavaged with the saline preparation, while the other was gavaged with the nanoparticle preparation. Blood was drawn, centrifuged, and counted for the following time points: baseline, 5 minutes, 15 minutes, 30 minutes, 60 minutes, 4 hours, and 24 hours.

Example 24

Intravenous Delivery of Radiolabeled Cholesterol Via Injection of Nanoparticle Preparation into the Heart A stock solution of tritiated cholesterol was counted and concluded to contain 15,000,000 DPM (disintegrations of isotope per minute). Each preparation was dialyzed before being used for the experiment. The dialyzed water was counted for DPMs lost in the dialysis water. The water was changed twice, and each time, 1.5 L of water was replaced, for a total of 3 L of water. In the first change, 221 DPM were counted in 1 mL of water. In the second change, 207 DPM were counted in 1 mL of water, for a total of 642,000 DPM lost in the dialysis water. The final nanoparticle preparation was counted and contained 3,000,000 DPM/mL. Saline preparations were made as controls for each nanoparticle preparation. Three mL of saline was added to 20 µL of tritiated cholesterol. When counted, this preparation was found to contain 9,800,000 DPM/mL. 500 µL of the previous saline preparation was added to 1.5 mL of saline. This contained 2,000,000 DPM/mL.

Figure 13:
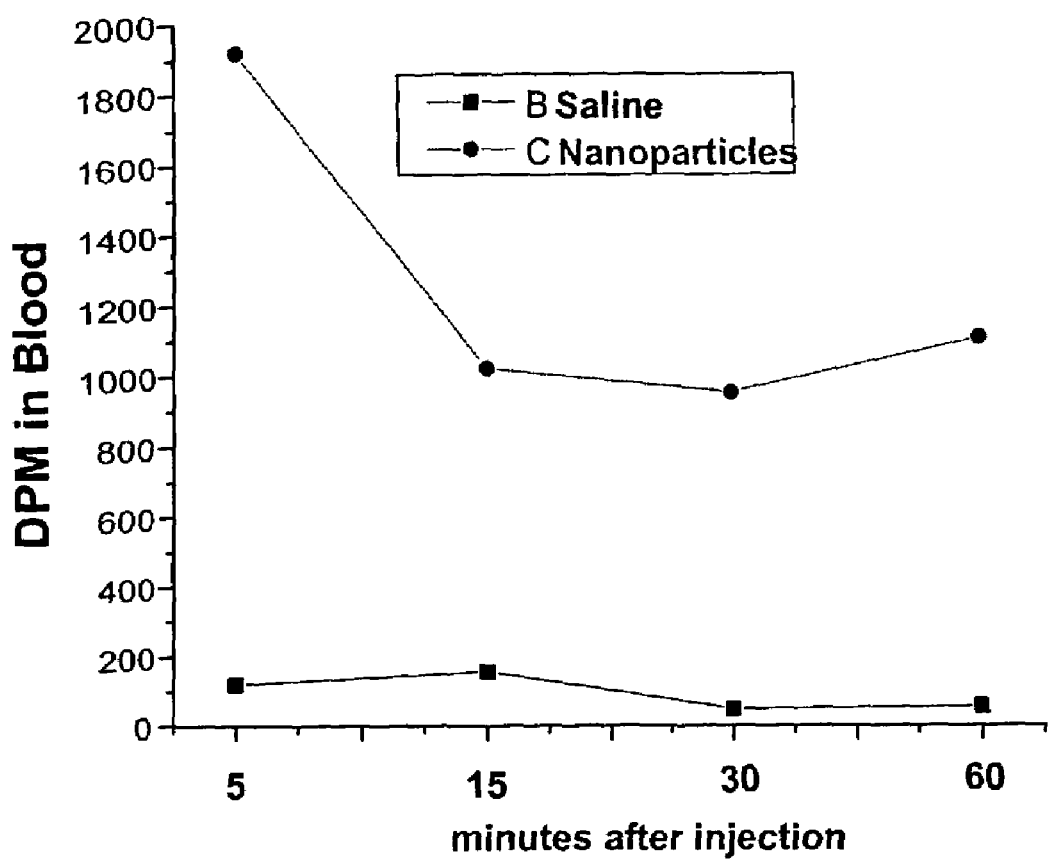
FIG. 13 is a plot of intra-venous delivery via the heart of tritiated cholesterol into rats.

Four rats were isolated for this experiment. Each rat received an injection of 1 mL of each solution directly into the heart. Blood samples were taken at time points 5 min, 15 min, 30 min, and 60 min. Results are shown in FIG. 13. As seen from the plot, cholesterol level in the blood was significantly higher (1200 DPM in 1 hour) following IV delivery of tritiated cholesterol using nanoparticles relative to the control, i.e., in saline (50 DPM in 1 hour). At the conclusion of the experiment, the animals were sacrificed and tissues were isolated for further analysis of the presence of tritiated cholesterol. The following tissues were isolated: liver, brain, heart, adrenal gland, kidney, and small intestine. These tissues were counted as the blood was counted, on a liquid scintillation counter.

Figure 14:
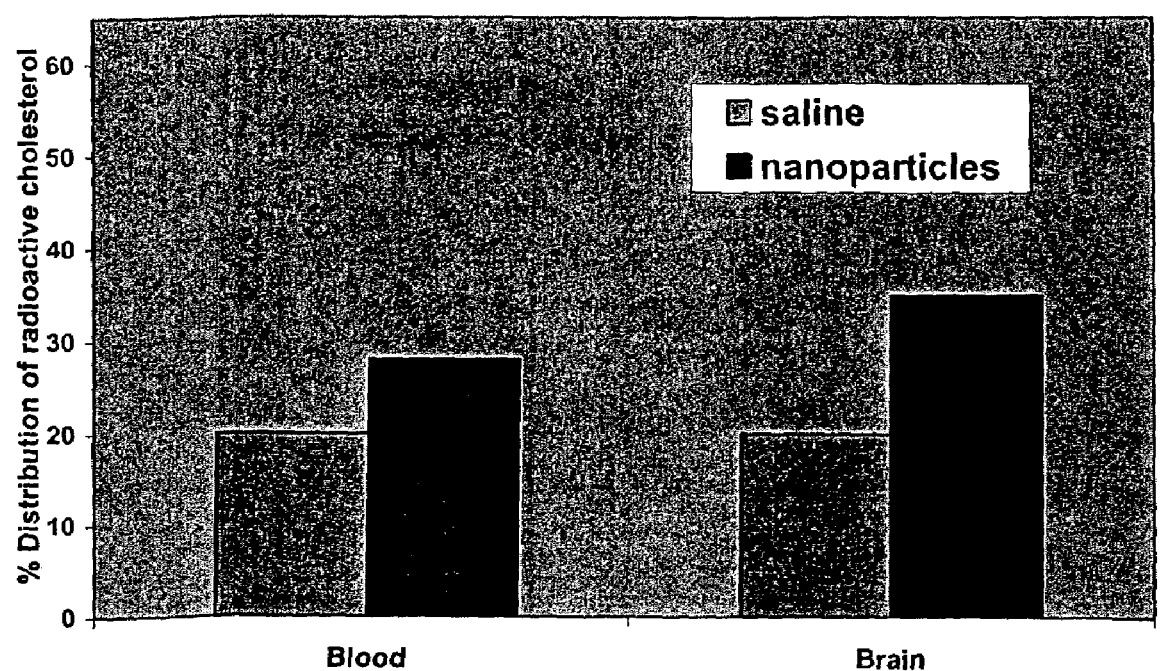
FIG. 14 is a bar graph that shows the distribution of radioactive cholesterol 24 hours after injection into a hamster heart, in saline and in nanoparticle form.
Figure 15:
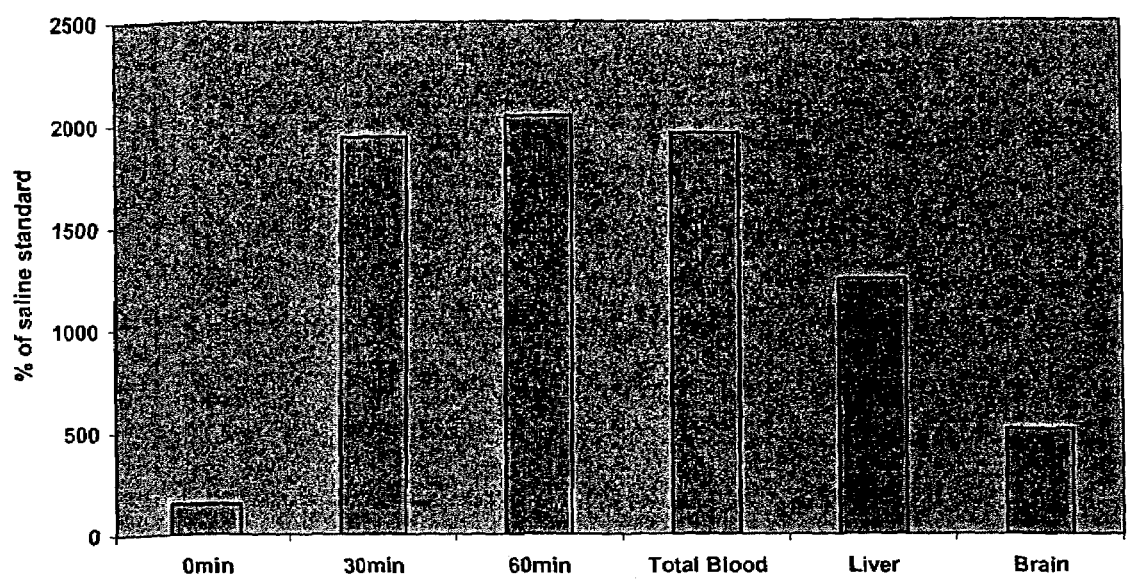
FIG. 15 is a bar graph that shows tritiated cholesterol distribution following oral administration, in saline and in nanoparticle form, expressed as a % of saline standard.

The results from the counts in the blood and brain are shown in FIG. 14. As seen from FIG. 14 cholesterol was delivered more effectively (40%) to the brain when delivered as a nanoparticle preparation, by crossing the blood brain barrier relative to control, i.e., delivered in saline (20%). FIG. 15 shows that cholesterol uptake in blood is rapid (delivery complete in one hour) when delivered by nanoparticles and further shows that cholesterol delivered as nanoparticles reaches the liver and brain.

Example 25

Particles with Antibacterial Properties

Cationic crosslinked hollow nanoparticles were prepared according to Example 21, and were tested against gram negative *Psedumonas Aeruginosa* and gram positive *Staphylococcus Aureus* bacteria. 3 mL of a nanoparticle solution was added to two plastic tubes and allowed to set and coat the tubes for ~26 hours. The nanoparticle solution was drained and 3 mL of a gram positive bacterial solution was added to one tube and 3 mL of a gram negative bacterial solution to the other tube. The control experiment was set up by adding 3 ml of the bacterial solutions to plastic tubes untreated with the nanoparticle solution. All four tubes were allowed to sit for 6 days to allow for formation of a biofilm on the walls of the tubes. At the end of 6 days, a bacterial stain was added to the four tubes. The presence of bacteria was tested using a microscope. No bacteria were present in the two tubes that had been previously treated with the nanoparticle solution, whereas bacteria were present in the two tubes not previously treated with the nanoparticle solution. The results demonstrate that the nanoparticles have antibacterial properties.

Example 26

Oxidation of Pullulan

Oxidized pullulan was obtained using standard oxidation techniques. For example, hydrolyzed pullulan ($M_n$=18,800) was dissolved in 200 ml water. Sodium bromide (1.6 g was added to the pullulan solution. The solution was cooled in an ice bath and 95 ml 5% sodium hypochlorite solution was added. Oxidation was initiated by adding 50 mg TEMPO. The pH of the solution was kept at 10.8 with 0.82 M sodium hydroxide solution. After 3 hours, 10 ml ethanol was added and the product was precipitated with acetone, filtered and washed with acetone. The product was dried in vacuum. The $^{13}$C NMR spectrum of the product indicated the presence of carboxyl groups (176 ppm), indicating the oxidation of the pullulan. A block copolymer of the oxidized pullanan and polycaprolactone was prepared in a similar manner as described in Example 8.

Example 27

Block Copolymer of Oxidized Pullulan and Polycaprolactone

Insulin (25 mg) was dissolved in 2.0 ml of methyl sulfoxide, and added to 50 mg of a copolymer of oxidized pullulan and polycaprolactone prepared according to method described in example 27. The mixture was stirred overnight. Water (10 ml) was added slowly, dropwise, and the solution was dialyzed against distilled water for 24 hours using a dialysis membrane of MWCO=6-8,000. The solution was filtered using a 0.45 micron syringe filter. The solution contained 15.6 microgram/ml insulin.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An amphiphilic linear block copolymer comprising a first polymer block and a second polymer block, wherein the first polymer block comprises a pullulan and the second polymer block is polycapralactone, polylactide, polyglycolide, or a copolymer thereof.

2. The copolymer of claim 1, wherein the copolymer forms micelles in a selective solvent.

3. The copolymer of claim 2, wherein the solvent comprises water, dimethyl sulfoxide, dimethyl acetamide, dimethyl formamide, chloroform, tetramethyl formamide, carbon tetrachloride, N-methylpyrrolidone, or dichloroethane.

4. A particle comprising the copolymer of claim 1, wherein the particle has a diameter of 1-1000 nanometers, measured in a dry state, and comprises a core made of one block of the copolymer and a shell made of another block of the copolymer.

5. The particle of claim 4, wherein the particle comprises a copolymer of a pullulan and a polycaprolactone.

6. The particle of claim 4, wherein the particle has a diameter of 15-100 nm, measured in a dry state.

7. The particle of claim 4, wherein the shell comprises the first polymer block.

8. The particle of claim 7, wherein the first polymer block is crosslinked.

9. A hollow particle comprising a shell comprising the first polymer block or the second polymer block of the amphiphilic linear block copolymer of claim 1, wherein the hollow particle has a diameter of 1-1000 nm, measured in a dry state.

10. A copolymer of claim 1, wherein the first polymer block is biologically active.

11. The copolymer of claim 10, wherein the biological activity of the first polymer block comprises antibacterial, antiviral, anticoagulative, anti-cancer, anti-proliferative, anti-atherosclerotic, anti-angiogenic, anti-metastatic, or cholesterol-lowering activity.

* * * * *